US011530257B2

(12) United States Patent
Jones et al.

(10) Patent No.: US 11,530,257 B2
(45) **Date of Patent: *Dec. 20, 2022**

(54) CHIMERIC ANTIBODIES FOR TREATMENT OF AMYLOID DEPOSITION DISEASES

(71) Applicant: The Trustees of Columbia University in the City of New York, New York, NY (US)

(72) Inventors: Tarran Jones, Radlett (GB); Alison Levy, Harpenden (GB); Siobhan O'Brien, Bishops Stortford (GB)

( * ) Notice: Subject to any disclaimer, the term of this patent is extended or adjusted under 35 U.S.C. 154(b) by 120 days.

This patent is subject to a terminal disclaimer.

(21) Appl. No.: 16/626,613

(22) PCT Filed: Jun. 28, 2018

(86) PCT No.: PCT/US2018/039905

§ 371 (c)(1),
(2) Date: Dec. 26, 2019

(87) PCT Pub. No.: WO2019/006062

PCT Pub. Date: Jan. 3, 2019

(65) Prior Publication Data

US 2020/0181246 A1 Jun. 11, 2020

Related U.S. Application Data

(60) Provisional application No. 62/526,835, filed on Jun. 29, 2017.

(51) Int. Cl.

| | |
|---|---|
| ***C07K 16/18*** | (2006.01) |
| ***A61K 38/00*** | (2006.01) |
| ***C12N 15/86*** | (2006.01) |

(52) U.S. Cl.

CPC .............. *C07K 16/18* (2013.01); *C12N 15/86* (2013.01); *A61K 38/00* (2013.01); *C07K 2317/24* (2013.01); *C07K 2317/34* (2013.01)

(58) Field of Classification Search

CPC ........................... C07K 16/18; C07K 2317/24; C07K 2317/34; A61K 38/00

See application file for complete search history.

(56) References Cited

U.S. PATENT DOCUMENTS

| | | | |
|---|---|---|---|
| 7,256,273 | B2 | 8/2007 | Basi et al. |
| 7,927,594 | B2 | 4/2011 | Rosenthal et al. |
| 8,105,594 | B2 | 1/2012 | Solomon et al. |
| 8,195,594 | B1 | 6/2012 | Bryce |
| 8,404,815 | B2 | 3/2013 | Schenk et al. |
| 8,591,894 | B2 | 11/2013 | Holzman et al. |
| 2009/0297439 | A1 | 12/2009 | Comoglio et al. |
| 2010/0150906 | A1 | 6/2010 | Pfeifer et al. |
| 2011/0177066 | A1 | 7/2011 | Schenk |
| 2013/0295082 | A1 | 11/2013 | Garidel et al. |
| 2016/0024197 | A1 | 1/2016 | Burbidge et al. |
| 2016/0243230 | A1 | 8/2016 | Wall et al. |

FOREIGN PATENT DOCUMENTS

| | | | |
|---|---|---|---|
| EA | 010902 | B1 | 12/2008 |
| EA | 015654 | B1 | 10/2011 |
| EP | 2730659 | A2 | 5/2014 |
| JP | 2009-530374 | A | 8/2009 |
| JP | 2017528449 | A | 9/2017 |
| RU | 2475500 | C2 | 2/2013 |
| RU | 2498999 | C2 | 11/2013 |
| WO | 9960024 | A1 | 11/1999 |
| WO | 1999060024 | A1 | 11/1999 |
| WO | 2003077858 | A2 | 9/2003 |
| WO | 2007108756 | A1 | 9/2007 |
| WO | 2007113172 | A2 | 10/2007 |
| WO | 2008011348 | A2 | 1/2008 |
| WO | 2016032949 | A1 | 3/2016 |
| WO | 2016187546 | A1 | 11/2016 |

OTHER PUBLICATIONS

The Extended European Search Report dated Mar. 11, 2021 for corresponding EP Application No. 18822805.0.

Langer AL et al. Results of phase 1 study of chimeric fibril-reactive monoclonal antibody 11-1 F4 in patients with AL amyloidosis. Blood, 2015, 126(23), 188, Meeting abstract 653. (Year: 2015).

Japanese Office Action for corresponding Japanese Application No. 2020-505320 dated Apr. 27, 2021.

Van Doren et al. Nonchemotherapy treatment of immunoglobulin light chain amyloidosis. Acta Haematol. 2020, 143:373-380. (Year:2020).

Extended European Search Report dated Apr. 23, 2021 for corresponding European Application No. 18 840 642.5.

Comenzo RL et al. Managing systemic light-chain amyloidosis. J. National Comprehensive Cancer Network, 2007, 5, 179-187. (Year: 2007).

Lin CY et al. Toxic human islet amyloid polypeptide (h-IAPP) oligomers are intracellular, and vaccination to induce anti-toxic oligomer antibodies does not prevent h-IAPP-induced beta-cell apoptosis in h-IAPP transgenic mice. Diabetes, 2007, 56, 1324-1332. (Year: 2007).

Lentzsch, Suzanne. Phase 1a/1 b study of 11-1 F4 mAb for the treatment of AL amyloidosis, 2015 NIH Grant# 1 RO 1 FD005110-01, retrieved from Grantome.com on Dec. 9, 2019. (Year: 2019).

Guidance for Industry: Estimating the maximum safe starting dose in initial clinical trials for therapeutics in adult healthy volunteers. US Dept. of Health and Human Service, Food and Drug Administration (FDA), Center for Drug Evaluation and Research (CDER), Jul. 2005, 30 pages. (Year: 2005).

(Continued)

*Primary Examiner* — Gregory S Emch

(74) *Attorney, Agent, or Firm* — McCormick, Paulding & Huber PLLC

(57) ABSTRACT

A chimeric mouse-human antibody for treatment of amyloid deposition diseases, pharmaceutical compositions comprising the antibody, methods and materials for producing the antibody, and methods for treating an amyloid deposition disease using the antibody and the pharmaceutical composition.

8 Claims, 8 Drawing Sheets

Specification includes a Sequence Listing.

(56) References Cited

OTHER PUBLICATIONS

Buss SJ et al. Longitudinal left ventricular function for prediction of survival in systemic light-chain amyloidosis. J. Amer. College Cardiology, 2012, 60(12), 1067-76. (Year: 2012).

Merlini G. AL amyloidosis: from molecular mechanisms to targeted therapies. Hematology Am Soc. Hematol. Educ. Program. Dec. 8, 2017, 2017(1): 1-12. (Year: 2017).

Edwards et al. "Analysis of the Phase 1 a/b Study of Chimeric Fibril-Reactive Monoclonal Antibody 11-1 F4 in Patients with AL Amyloidosis," Blood, Dec. 1, 2016 (Dec. 1, 2016), vol. 128, No. 22, p. 643. entire document.

Solomon A. et al. Therapeutic potential of chimeric amyloidreactive monoclonal antibody 11-1F4 // Clinical cancer research.—2003.—V. 9.—No. 10.—p. 3831s-3838s. [НаЙД e$_{H}$o Jun. 3, 2020], URL: https://clincancerres.aacrjournals.org/content/9/10/3831s.

Edwards C. V. et al. Interim analysis of the phase 1a/b study of chimeric fibril-reactive monoclonal antibody 11-1F4 in patients with AL amyloidosis // Amyloid.—2017.—V. 24.—No. sup1.—p. 58-59. [НаЙД e$_{H}$o Jun. 3, 2020], URL: https://www.tandfonline.com/doi/abs/10.1080/13506129.2017.1292900.

International Search Report for PCT Application No. PCT/US2018/039905 dated Sep. 24, 2018.

Russian Search Report for corresponding Russian Application No. 2019141754 dated Jun. 3, 2020.

Merlini G. et al., Molecular mechanisms of amyloidosis, N. Engl. J. Med., 2003, vol. 349, Issue 6, pp. 583-596.

Tuzovic M. et al. Cardiac Amyloidosis: Diagnosis and Treatment Strategies, Curr Oncol Rep., 2017, vol. 19, Issue 7, p. 46.

Riechmann L. et al., Reshaping human antibodies for therapy, Nature, 1988, vol. 332, Issue 6162, pp. 323-327.

Vajdos F.F. et al., Comprehensive Functional Maps of the Antigenbinding Site of an Anti-ErbB2 Antibody Obtained with Shotgun Scanning Mutagenesis, J. Mol. Biol., 2002, vol. 320, pp. 415-428.

De Pascalis R. et al., Grafting of "abbreviated" complementarity-determining regions containing specificity-determining residues essential for ligand contact to engineer a less immunogenic humanized monoclonal antibody, J Immunol., 2002, vol. 169, Issue 6, pp. 3076-3084.

Desport, E., et al. "AL-Amyloidosis" pp. 36-50.

Russian Search Report for corresponding Russian Application No. 2020108100 dated Oct. 7, 2020.

Australian Examination Report for corresponding Australian Application No. 2018290898 dated Nov. 12, 2020.

Wall, Jonathan, "Radioimmunodetection of amyloid deposits in patients with AL amyloidosis", Blood, 2010, vol. 116, No. 13, pp. 2241-2244.

Japanese Office Action dated Dec. 15, 2020 for corresponding Japanese Application No. 2019-572403.

Study of Chimeric Fibril-Reactive Monoclonal Antibody 11-1 F4 in Patients with AL Amyloidosis, ClinicalTrials.gov, Identifier: NCT02245867, first posted Sep. 22, 2014, retrieved from internet Dec. 9, 2019. (Year: 2014).

Examination Report in corresponding Australian Application No. 2018311688 dated Feb. 16, 2021.

Lavatelli, et al., Biochemical markers in early diagnosis and management of systemic amyloidoses. Clin. Chem. Lab Med. 2014, 52 (11):1517-1531. (Year: 2014).

Moghimi et al. "High Efficiency Ex Vivo Gene Transfer to Primary Murine B Cells Using Plasmid or Viral Vectors." J Genet Syndr Gene Ther. vol. 2, No. 103. Apr. 3, 2013. 10 pages. doi:10.4172/2157-7412.1000103.

Colombian Office Action received Jul. 19, 2022, in connection with corresponding CO Application No. NC2020/0000260 (12 pp., including machine-generated English translation).

Japanese Office Action received Jul. 26, 2022, in connection with corresponding JP Application No. 2021-523841 (10 pp., including machine-generated English translation).

Figure 2

```
        10                30                50
caggtgcagctgaaggagtcaggacctggcctggtggcgccctcacagagcctgtccatc
---------+---------+---------+---------+---------+---------+
gtccacgtcgacttcctcagtcctggaccggaccaccgcgggagtgtctcggacaggtag
Q  V  Q  L  K  E  S  G  P  G  L  V  A  P  S  Q  S  L  S  I

        70                90               110
                           -----CDR1------
acatgcactgtctcagggttctcattaagcagctatggtgtaagctgggttcgccagcct
---------+---------+---------+---------+---------+---------+
tgtacgtgacagagtcccaagagtaattcgtcgataccacattcgacccaagcggtcgga
T  C  T  V  S  G  F  S  L  S  S  Y  G  V  S  W  V  R  Q  P

       130               150               170
                         ---------------------------------
ccaggaaagggtctggagtggctgggagtaatatggggtgacgggagcacaaattatcat
---------+---------+---------+---------+---------+---------+
ggtcctttcccagacctcaccgaccctcattataccccactgccctcgtgtttaatagta
P  G  K  G  L  E  W  L  G  V  I  W  G  D  G  S  T  N  Y  H

       190               210               230
------CDR2-------------------
ccaaatctcatgtccagactgagtatcagcaaggatatttccaagagccaagttctcttc
---------+---------+---------+---------+---------+---------+
ggtttagagtacaggtctgactcatagtcgttcctataaaggttctcggttcaagagaag
P  N  L  M  S  R  L  S  I  S  K  D  I  S  K  S  Q  V  L  F

       250               270               290
                                                 --CDR3---
aaactgaatagtctgcaaactgatgacacagccacgtactactgtgtcaccttggactac
---------+---------+---------+---------+---------+---------+
tttgacttatcagacgtttgactactgtgtcggtgcatgatgacacagtggaacctgatg
K  L  N  S  L  Q  T  D  D  T  A  T  Y  Y  C  V  T  L  D  Y

       310               330
tggggtcaaggaacctcagtcaccgtctcctca
---------+---------+---------+---
accccagttccttggagtcagtggcagaggagt
W  G  Q  G  T  S  V  T  V  S  S
```

Figure 3

```
        10                  30                  50
gatgttgtgatgacccaaactccactctccctgcctgtcagtcttggagatcaagcctcc
---------+---------+---------+---------+---------+---------+
ctacaacactactgggtttgaggtgagagggacggacagtcagaacctctagttcggagg
D  V  V  M  T  Q  T  P  L  S  L  P  V  S  L  G  D  Q  A  S

        70                  90                 110
         -------------------------CDR1-------------------
atctcttgcagatctagtcagagccttgtacatagaaatggaaacacctatttacattgg
---------+---------+---------+---------+---------+---------+
tagagaacgtctagatcagtctcggaacatgtatctttacctttgtggataaatgtaacc
I  S  C  R  S  S  Q  S  L  V  H  R  N  G  N  T  Y  L  H  W

       130                 150                 170
                                          -----------CDR2---
tacctgcagaagccaggccagtctccaaagctcctgatctacaaagtttccaaccgattt
---------+---------+---------+---------+---------+---------+
atggacgtcttcggtccggtcagaggtttcgaggactagatgtttcaaaggttggctaaa
Y  L  Q  K  P  G  Q  S  P  K  L  L  I  Y  K  V  S  N  R  F

       190                 210                 230

tctggggtcccagacaggttcagtggcagtggatcagggacagatttcacactcaagatc
---------+---------+---------+---------+---------+---------+
agaccccagggtctgtccaagtcaccgtcacctagtccctgtctaaagtgtgagttctag
S  G  V  P  D  R  F  S  G  S  G  S  G  T  D  F  T  L  K  I

       250                 270                 290
                                       --------------CDR3---
agcagagtggaggctgaggatttgggactttatttctgttttcaaactacatatgttccg
---------+---------+---------+---------+---------+---------+
tcgtctcacctccgactcctaaaccctgaaataaagacaaaagtttgatgtatacaaggc
S  R  V  E  A  E  D  L  G  L  Y  F  C  F  Q  T  T  Y  V  P

       310                 330
------
aacacgttcggaggggggaccaagctggaaataaaa
---------+---------+---------+------
ttgtgcaagcctcccccctggttcgacctttatttt
N  T  F  G  G  G  T  K  L  E  I  K
```

Figure 5

```
5'-aagcttgccgccaccatgaagttgcctgttaggctgttggtgc-3'

HindIII  Kozak                  Leader
aagcttgccgccaccatgaagttgcctgttaggctgttggtgctgatgttctggattcctgcttccagcagt
-+---------+---------+---------+---------+---------+---------+---------+
ttcgaacggcggtggtacttcaacggacaatccgacaaccacgactacaagacctaaggacgaaggtcgtca
               M  K  L  P  V  R  L  L  V  L  M  F  W  I  P  A  S  S  S

         10                  30                  50
gatgttgtgatgacccaaactccactctccctgcctgtcagtcttggagatcaagcctcc
---------+---------+---------+---------+---------+---------+
ctacaacactactgggtttgaggtgagagggacggacagtcagaacctctagttcggagg
D  V  V  M  T  Q  T  P  L  S  L  P  V  S  L  G  D  Q  A  S

         70                  90                 110
         -------------------------CDR1-------------------
atctcttgcagatctagtcagagccttgtacatagaaatggaaacacctatttacattgg
---------+---------+---------+---------+---------+---------+
tagagaacgtctagatcagtctcggaacatgtatctttacctttgtggataaatgtaacc
I  S  C  R  S  S  Q  S  L  V  H  R  N  G  N  T  Y  L  H  W

        130                 150                 170
                                                 -----------CDR2---
tacctgcagaagccaggccagtctccaaagctcctgatctacaaagtttccaaccgattt
---------+---------+---------+---------+---------+---------+
atggacgtcttcggtccggtcagaggtttcgaggactagatgtttcaaaggttggctaaa
Y  L  Q  K  P  G  Q  S  P  K  L  L  I  Y  K  V  S  N  R  F

        190                 210                 230

tctggggtcccagacaggttcagtggcagtggatcagggacagatttcacactcaagatc
---------+---------+---------+---------+---------+---------+
agaccccagggtctgtccaagtcaccgtcacctagtccctgtctaaagtgtgagttctag
S  G  V  P  D  R  F  S  G  S  G  S  G  T  D  F  T  L  K  I

        250                 270                 290
                                              --------------CDR3---
agcagagtggaggctgaggatttgggactttatttctgtttcaaactacatatgttccg
---------+---------+---------+---------+---------+---------+
tcgtctcacctccgactcctaaaccctgaaataaagacaaagtttgatgtatacaaggc
S  R  V  E  A  E  D  L  G  L  Y  F  C  F  Q  T  T  Y  V  P

        310                 330
------                                           BamHI
aacacgttcggagggggggaccaagctggaaatcaaacgtgagtggatcc
---------+---------+---------+---------+---------
ttgtgcaagcctccccccctggttcgacctttagtttgcactcacctagg
N  T  F  G  G  G  T  K  L  E  I  K

    3 -agcctccccccctggttcgacctttagtttgcactcacctagg-5
```

```
5'-aagctttccgccaccatggctgtcctggggctgctcttctgc-3'

HindIII Kozak                        Leader
aagcttgccgccaccatggctgtcctggggctgctcttctgcctggtgacattcccaagctgtgtcctgtcc
-+---------+---------+---------+---------+---------+---------+---------+
ttcgaacggcggtggtaccgacaggaccccgacgagaagacggaccactgtaagggttcgacacaggacagg
                 M   A   V   L   G   L   L   F   C   L   V   T   F   P   S   C   V   L   S

          10                    30                    50

caggtgcagctgaaggagtcaggacctggcctggtggcgccctcacagagcctgtccatc
---------+---------+---------+---------+---------+---------+
gtccacgtcgacttcctcagtcctggaccggaccaccgcgggagtgtctcggacaggtag
Q   V   Q   L   K   E   S   G   P   G   L   V   A   P   S   Q   S   L   S   I

          70                    90                   110
                                   -----CDR1------
acatgcactgtctcagggttctcattaagcagctatggtgtaagctgggttcgccagcct
---------+---------+---------+---------+---------+---------+
tgtacgtgacagagtcccaagagtaattcgtcgataccacattcgacccaagcggtcgga
T   C   T   V   S   G   F   S   L   S   S   Y   G   V   S   W   V   R   Q   P

         130                   150                   170
                               -----------------------------
ccaggaaagggtctggagtggctgggagtaatatggggtgacgggagcaccaattatcat
---------+---------+---------+---------+---------+---------+
ggtcctttcccagacctcaccgaccctcattataccccactgccctcgtggttaatagta
P   G   K   G   L   E   W   L   G   V   I   W   G   D   G   S   T   N   Y   H

         190                   210                   230
------CDR2-------------------
ccaaatctcatgtccagactgagtatcagcaaggatatttccaagagccaagttctcttc
---------+---------+---------+---------+---------+---------+
ggtttagagtacaggtctgactcatagtcgttcctataaaggttctcggttcaagagaag
P   N   L   M   S   R   L   S   I   S   K   D   I   S   K   S   Q   V   L   F

         250                   270                   290
                                                   --CDR3---
aaactgaatagtctgcaaactgatgacacagccacgtactactgtgtcaccttggactac
---------+---------+---------+---------+---------+---------+
tttgacttatcagacgtttgactactgtgtcggtgcatgatgacacagtggaacctgatg
K   L   N   S   L   Q   T   D   D   T   A   T   Y   Y   C   V   T   L   D   Y

         310                   330
                                       ----------CH1---------→
tggggtcaaggaacctcagtcaccgtctcctcagcctccaccaagggcccatcgg
---------+---------+---------+---------+---------+=====
accccagttccttggagtcagtggcagaggagtcggaggtggttcccgggtagcc
W   G   Q   G   T   S   V   T   V   S   S
                                                  ApaI

    3 -ccttggagtcagtggcagaggagtcggaggtggttcccgggtagcc-5
```

CHIMERIC ANTIBODIES FOR TREATMENT OF AMYLOID DEPOSITION DISEASES

CROSS-REFERENCE TO RELATED APPLICATIONS

This application is a National Stage application of International Patent Application No. PCT/EP2016/082128, filed on Dec. 21, 2016, which claims priority from U.S. provisional patent application 62/526,835, filed Jun. 29, 2017, each of which is incorporated herein by reference in its entirety.

GOVERNMENT RIGHTS

This invention was made with U.S. government support under CA020056 awarded by the National Institutes of Health. The government has certain rights in the invention.

REFERENCE TO A SEQUENCE LISTING SUBMITTED BY EFS-WEB

The contents of the ASCII text file of the sequence listing named "8441-0004-1_ST25", which is 15.6 kb in size, was created on Jun. 4, 2018, and electronically submitted via EFS-Web with this application is incorporated herein by reference in its entirety.

TECHNICAL FIELD

The present invention relates to chimeric mouse-human antibodies useful to treat amyloid deposition diseases, particularly primary (AL) amyloidosis, pharmaceutical compositions comprising such antibodies, methods and materials for preparing such antibodies, and methods of treating amyloid deposition diseases using said antibodies and pharmaceutical compositions.

BACKGROUND

Native antibodies are usually heterotetrameric glycoproteins of about 150,000 daltons composed of two identical light chains and two identical heavy chains. Each light chain is linked to a heavy chain by one disulfide bond, while the number of additional disulfide linkages between the heavy chains varies with different antibody isotypes. The simplest isotype is IgG, which comprises just two light chains and two heavy chains, in which the two heavy chains are linked by two disulfide linkages. Each heavy chain has a variable domain ($V_H$) at one end with a number of adjacent constant domains. Each light chain has a variable domain ($V_L$) at one end and a constant domain at its other end. Each variable domain of the light and heavy chain in an antibody comprises three segments called complementarity-determining regions ("CDR") or hypervariable regions. Each CDR in a light chain, together with the corresponding CDR in the adjacent heavy chain, form an antigen-binding site of the antibody. Light chains are of two major types, K and A, depending on their constant region. Both K and A light chains may combine with any of the different heavy chain types.

Amyloid light-chain amyloidosis (AL amyloidosis), also called primary amyloidosis, is the most common form of systemic amyloidosis in the United States. The term "amyloidosis" refers to a cluster of diseases which share a common feature, i.e, the extracellular deposition of pathologic insoluble fibrillar proteins in organs and tissues (Rodney, et al.—*NEJM,* 25:898). Amyloidosis is caused by malfunction of a person's antibody-producing cells causing production of abnormal protein fibers which aggregate to form insoluble amyloid deposits in organs and tissues. The type of amyloidosis is determined by the nature of the precursor proteins which form the fibril deposit. In primary amyloidosis (AL), the fibrils comprise fragments of immunoglobulin light chains and in secondary amyloidosis, the fibrils comprise amyloid A protein. Modern classification of amyloidosis is based on the nature of the precursor plasma proteins which form the fibril deposit.

The precursor plasma proteins are diverse and unrelated. Nevertheless, all precursor deposits produce amyloid deposits which share a common typical β-pleated-sheet configuration, which is responsible for the typical staining properties of the fibrillar deposits. The final stage in the development of amyloidosis is the deposit of amyloid fibrils in the organs of the sufferer. Amyloidosis mortality is high, with current five-year survival rates of about 28%.

To date, the treatment of AL has been directed towards reducing the synthesis of amyloidogenic precursor light chains by attacking the malfunctioning cells through conventional or high dose cytotoxic chemotherapy. This treatment suffers from two disadvantages. First, the fibrillar deposits are often asymptomatic until after significant deposition has taken place. Therefore, treatment is unlikely to be undertaken before significant deposits have already occurred. Second, since this treatment is at best effective only to stop the production of precursor abnormal protein but not to remove the existing deposits, prognosis for AL patients remains exceedingly poor due to persistence (or progression) of the pathologic deposits (Solomon, et al.—*Int. J. Exp. Clin. Invest.* 2:269)

Recent animal studies have shown that the administration of the murine 11-1F4 antibody and other murine anti-human light chain specific antibodies directed against an epitope common to the β-pleated-sheet structure present on AL fibrils results in complete degradation of the human ALκ and ALλ amyloid deposits. Some of these murine antibodies are described in U.S. Pat. No. 8,105,594, which is incorporated herein by reference in its entirety.

Murine antibodies are generally unsuitable for administration to other animal species (such humans) because the receiving species will recognize the murine antibody as antigenic and will produce antibodies against it. The antigenicity of an antibody from one species when injected into another species is normally caused by a portion of a constant domain. Such an antigenic response will impede or prevent the desired therapeutic effect of the murine antibody. In humans, this antigenic response is called human anti-mouse antibody (HAMA). The antibodies described in the '594 patent have the potential to be highly immunogenic in humans via the human anti-mouse antibody (HAMA) response. Since the HAMA response usually results in the rapid clearance of a mouse antibody from the human recipient, HAMA would severely limit any potential human therapeutic benefit a murine antibody could have. Therefore, these murine antibodies are unsuitable for administration to a patient to halt or reverse the deposition of amyloid fibrils in a patient and a need exists for an antibody treatment for amyloid deposition diseases that has low immunogenicity in humans.

SUMMARY

One embodiment of the invention is chimeric mouse-human antibodies useful for treatment of amyloid deposition diseases, particularly primary (AL) amyloidosis.

Another embodiment of the invention is a pharmaceutical composition comprising the chimeric antibody and a pharmaceutically acceptable carrier.

Another embodiment of the invention is methods and materials for producing such antibodies, including polynucleotide sequences and vector constructs.

Another embodiment of the invention is methods for treating or ameliorating the symptoms of amyloid deposition diseases, such as primary (AL) amyloidosis, in a human in need of such treatment by administering to a human patient in need of such treatment or amelioration an effective amount of at least one of such antibodies effective to treat or ameliorate the symptoms of said amyloid deposition disease, together with a pharmaceutically acceptable carrier.

Another embodiment of the invention is a method of detection of an amyloid deposition disease in a patient suspected of having such disease by administering a labeled antibody of the invention and detecting the presence of the label in the patient. The label may be a radiolabel, such as $^{124}$I, but other sorts of labels can be readily envisioned by one of skill in the art. Included in this embodiment is the labeled antibody itself.

BRIEF DESCRIPTION OF THE DRAWINGS

FIG. 2 is a listing of DNA and amino acid sequences of the murine 11-1F4 antibody $V_H$ region gene, SEQ ID NO: 39 and NO: 35, respectively.

FIG. 3 is a listing of DNA and amino acid sequences of the murine 11-1F4 antibody $V_K$ region gene, SEQ ID NO: 40 and NO: 36, respectively.

FIG. 5 is a map of the immunoglobulin gamma 1 heavy chain expression vector pG1D200. It consists of a pSV2dhfr vector fragment, which has the SV40 early and crippled SV40 late promoter, the SV40 origin, and the Co1E1 origin. It also has the ampicillin resistance and dhfr genes. The crippled SV40 late promoter drives the dhfr gene. Consequently, expression is poor, allowing for the selection of multigene/high expression level clones using comparatively low levels of methotrexate. It also has the HCMVi promoter fragment, a multiple cloning site, cDNA for a human gamma 1 constant region gene (intron minus) which is followed by a spaC2 termination signal sequence ("Amie").

FIG. 6 is a listing of the DNA and amino acid sequences of the modified murine 11-1F4 antibody $V_K$ region gene (SEQ ID NO: 42 and NO: 47, respectively) and the sequences of the oligonucleotide primers used to modify the $V_K$ gene (SEQ ID NO: 41 and NO: 43, respectively), as well as the DNA sequence with leader (SEQ ID NO: 37).

FIG. 7 is a listing of the DNA and amino acid sequences of the modified murine 11-1F4 antibody $V_H$ region gene (SEQ ID NO: 45 and NO: 48, respectively) and the sequences of the oligonucleotide primers used to modify the $V_H$ gene (SEQ ID NO: 44 and NO: 46, respectively), as well as the DNA sequence with leader (SEQ ID NO: 38).

Figure 1:
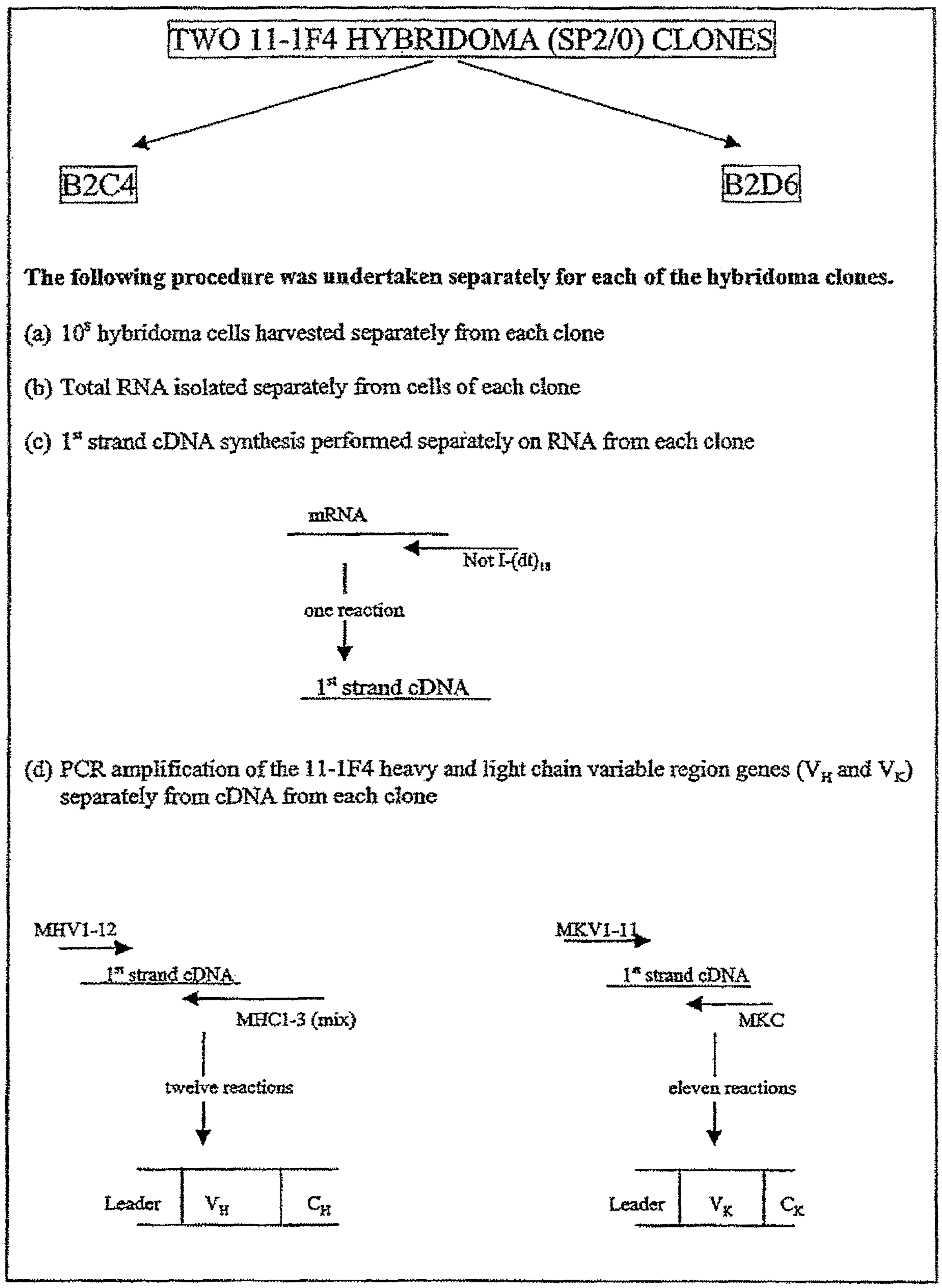
FIG. 1 outlines the strategy used to clone the murine $V_H$ and $V_K$ genes from a hybridoma cell line.

New sv=pG1KD200-11-1F4.

New co-transfection =11-1F4VHpG1D200 plus 11-1F4VK.pKN100.

DETAILED DESCRIPTION

In accordance with the present invention, chimeric mouse-human antibodies are provided that are useful for administration to humans suffering from amyloid deposition diseases to treat or ameliorate the symptoms of the disease. The chimeric antibodies of the invention bind to amyloid deposits and activate the patient's immune system to clear the bound materials while producing little or no HAMA reaction. The invention also provides pharmaceutical compositions comprising at least one of said chimeric antibodies and a pharmaceutically acceptable carrier, methods and materials for producing these antibodies, and methods of treating or ameliorating the symptoms of a patient suffering from amyloidosis by administering to the patent an amount of the chimeric antibody effective to remove at least some of the amyloid deposits from the patient's organs and thus to treat or ameliorate the symptoms of the amyloidosis.

In the present invention, at least one chimeric antibody is administered to a human patient suffering from amyloidosis to promote the degradation and removal of at least some of the amyloid fibrils which have become deposited in the organs of the patient. A therapeutically effective amount of the antibody is administered together with a pharmaceutically acceptable carrier. Suitable pharmaceutically acceptable carriers are well-known in the art. A typical route of administration is parenterally (e.g., intravenously), as is well understood by those skilled in the medical arts. Other routes of administration are of course possible. Administration may be by single or multiple doses. The amount of antibody administered and the frequency of dosing may be optimized by the physician for the particular patient.

The therapeutically effective dose of antibody administered to the patient (whether administered in a single does or multiple doses) should be sufficient to reduce the amount of deposited amyloid fibrils in the patient. Such therapeutically effective amount may be determined by evaluating the symptomatic changes in the patient or by evaluating the change in the amount of deposited amyloid fibrils (e.g., by radioimmune detection of deposited amyloid deposits using $^{124}$I tagged antibody). Thus, labeled antibody of the invention may be used to detect the presence of amyloid deposition disease on a patient suspected of having the disease as well as to determine the effectiveness of treatment.

To produce the chimeric antibodies of the invention, the murine 11-1F4 monoclonal antibody heavy and kappa light chain variable region genes described in U.S. Pat. No. 8,105,594 were PCR modified to facilitate the expression of the chimeric 11-1F4 antibody in mammalian cells. A detailed sequence analysis of the modified variable region genes was performed. The modified variable region genes were cloned into the appropriate mammalian expression vectors, creating the constructs 11-1F4VHpG1D200 and 11-1F4VK.pKN100. A single supervector construct, pG1KD200-11-1F4, was made from the 11-1F4VHpG1D200 and 11-IF4VK.pKN100 constructs by EcoRI restriction enzyme digest and ligation. Finally, the chimeric 11-1F4 antibody was transiently expressed in COS cells by both cotransfection and single supervector transfection. While COS cells were chosen for the co-transfection or transfection as a matter of convenience, those of skill in the art would recognize that other mammalian cell lines could be used. The characterization of the binding capacity of the chimeric 11-1F4 antibody for amyloid fibrils was determined by direct binding ELISA. Unexpectedly and beneficially, the chimeric 11-1F4 antibody bound to amyloid fibrils with higher affinity than the murine 11-1F4 antibody.

The antibody of the invention comprises a chimeric mouse-human monoclonal antibody comprising the $V_K$ region of SEQ ID NO: 47 and the $V_H$ region of SEQ ID NO: 48. This antibody binds to an epitope expressed by the β-pleated sheet configuration of amyloid fibrils. Moreover, surprisingly the antibody binds to this epitope with higher affinity than the 11-1F4 mouse antibody from which it was derived, which comprises the $V_K$ region of SEQ ID NO: 36 and the $V_H$ region of SEQ ID NO: 35. The invention includes methods of treating an amyloid deposition disease in a human patient in need of such treatment which comprises administering to the patient the above antibody in a pharmaceutically-acceptable carrier. The amount of antibody administered should be effective to reduce the amount of amyloid fibrils deposited in the tissues of the patient. The antibody composition may be administered by any conventional route of administration, but parenteral administration (such as intravenous) is preferred. Pharmaceutically-acceptable carriers are well-known in the art and a suitable one can be selected by one of skill in the medical field. The amyloid deposition disease is preferably primary (AL) amyloidosis.

Figure 5:
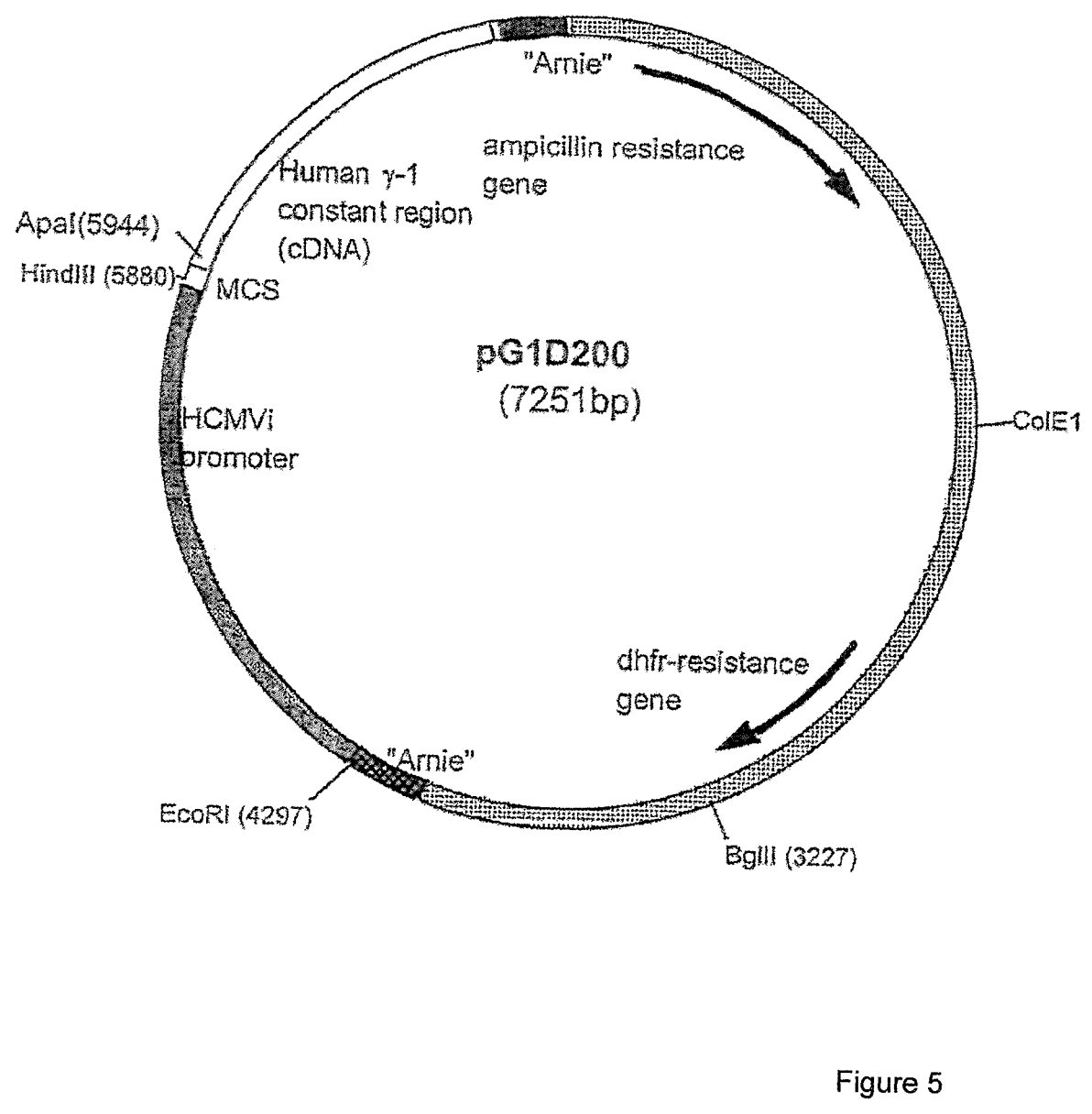

The invention also includes methods and materials for making the subject antibody. Materials useful to make the subject antibody include vector constructs selected from the group consisting of 11-1F4VK.pKN100 and 11-F4VH.pG1D200, shown in FIGS. 5 and 6, respectively, and the superconstruct pG.1KD20011-1F4 made from the two above vector constructs. Other useful materials include the modified murine 11-1F4 antibody $V_K$ region gene (SEQ ID NO: 42) and the modified 11-1F4 antibody $V_H$ region gene (SEQ ID NO: 45), as well as the respective primers SEQ ID NO: 41, 43, 44, and 46. The subject antibody may be made by co-transfection of the vector constructs 11-1F4VK.pKN100 and 11-F4VH.pG1D200 or the superconstruct pG.1KD20011-1F4 in a suitable mammalian host cell, such as COS (Chinese hamster ovary) cells.

Abbreviations

Dulbecco's Modified Eagles Medium (DMEM), Fetal Bovine Serum (FBS), ribonucleic acid (RNA); messenger RNA (mRNA); deoxyribonucleic acid (DNA); copy DNA (cDNA); polymerase chain reaction (PCR); minute (min); second (sec); Tris-borate buffer (TBE).

Amino acids are represented by the IUPAC abbreviations, as follows: Alanine (Ala A), Arginine (Arg; R), Asparagine (Asn; N), Aspartic acid (Asp; D), Cysteine (Cys; C), Glutamine (Gln; Q), Glutamic acid (Glu; E), Glycine (Gly; G), Histidine (His; H), Isoleucine (Ile; I), Leucine (Leu; L), Lysine (Lys; K), Methionine (Met; M), Phenylalanine (Phe; F), Proline (Pro; P), Serine (Ser; S), Threonine (Thr; T), Tryptophan (Trp; W), Tyrosine (Tyr; Y), Valine (Val; V). Similarly for nucleotides: Adenine (a), Cytosine (c), Guanine (g), Thymine (t), Uracil (u) ,Adenine or Guanine (r), Cytosine or Thymine (y), Guanine or Cytosine (s), Adenine or Thymine (w), Guanine or Thymine (k), Adenine or Cytosine (m), Cytosine or Guanine or Thymine (b), Adenine or Guanine or Thymine (d), Adenine or Cytosine or Thymine (h), Adenine or Cytosine or Guanine (v), and any base (n).

EXAMPLE 1

PCR Cloning and DNA Sequencing of the mouse 11-1F4 Antibody

The murine 11-1F4 monoclonal antibody heavy and light chain variable region genes were PCR cloned and a detailed sequence analysis of all variable region genes isolated (both pseudo and functional) was performed. Detailed DNA and amino acid sequences of the murine 11-1F4 heavy and light chain variable region genes were obtained.

Materials

Media components and all other tissue culture materials were obtained from Life Technologies (UK). The RNA solution kit was obtained from Stratagene (USA), while the first strand cDNA synthesis kit was purchased from Pharmacia (UK). All the constituents and equipment for the RCR-reaction, including AmpliTaq® DNA polymerase, were purchased from Perkin Elmer (USA). The TOPO TA Cloning ® kit was obtained from Invitrogen (USA). Agarose (UltraPure™) was obtained from Life Technologies (UK). The ABI PRISM® Big Dye™ terminator cycle sequencing ready reaction kit pre-mixed cycle sequencing kit and the ABI PRISM® 310 sequencing machine were both purchased from PE Applied Biosystems (USA). All other molecular biological products were obtained from New England Biolabs (USA) and Promega (USA).

Methods

The strategy used to PCR clone the murine $V_H$ and $V_K$ genes from the hybridoma cell lines producing the murine monoclonal antibody 11-1F4 is outlined in FIG. 1.

Two clones (B2C4 and B2D6) of the SP2/0 hybridoma cell line producing the α-human light chain monoclonal antibody 11-1F4, were kindly provided by Alan Solomon, MD (University of Tennessee Medical Center at Knoxville, Tenn.). The hybridoma cell line is available from the American Type Culture Collection (ATCC access PTA-105). The cell lines were cultured using DMEM media supplemented with 20% (v/v) FBS, penicillin/streptomycin and L-Glutamine. Cells were cultured until a total viable cell count of $10^8$ cells was reached.

The cells were harvested separately from each clone as follows. The mouse hybridoma cell line was grown in suspension in an appropriate culture medium and in sufficient quantities to provide a total viable cell count of about $10^8$ cells. The culture supernatant was harvested and the hybridoma cells pelleted in a bench top centrifuge (250 g, 5 min). The cells were gently re-suspended in 20 ml PBS and a 100 μl aliquot was taken for a viable cell count. The cells in the aliquot were pelleted once more and 200 μl of PBS and 200 μl of trypan blue were added to the 100 μl of cells and mixed gently. Ten μl of this mixture was pipetted into a disposable cell-counting slide and the number of white cells in 9 small squares was counted under a microscope. Blue cells (i.e. dead cells) were not counted. The count process was repeated, the results averaged, and the average results multiplied by $9\times10^5$ to obtain a viable cell count for the cells in 20 ml PBS. Once sufficient cells had been harvested, they were re-suspended in 10 ml of Solution D for RNA isolation (see below, Stratagene RNA Isolation Kit).

Total RNA was then isolated separately from the cells of each clone using a Stratagene RNA isolation kit, according to the manufacturer's instructions. One ml of 2 M sodium acetate (pH 4.0) was added to the sample and the contents of the tube were thoroughly mixed by repeatedly inverting the tube. To the tube was added 10.0 ml of phenol (pH 5.3-5.7) and the contents again mixed thoroughly by inversion. To the mixture was added 2.0 ml of chloroform-isoamyl alcohol mixture, the tube was capped and vigorously shaken for 10 seconds, and the tube was incubated in ice for 15 minutes. The sample was transferred to a 50-ml thick-walled, round-bottom centrifuge tube that had been pre-chilled on ice and the tube was spun in a centrifuge at 10,000×g for 20 minutes at 4° C. Two phases were visible in the tube after centrifugation. The upper, aqueous phase contained the RNA, while the lower phenol phase and interphase contained DNA and proteins. The RNA-containing upper, aqueous phase was transferred to a fresh centrifuge tube and the lower phenol phase was discarded. An equal volume of isopropanol was added to the aqueous phase and the contents mixed by inversion, following which the tube was incubated for 1 hour at −20° C. to precipitate the RNA. The tube was spun in a centrifuge at 10,000×g for 20 minutes at 4° C. After centrifugation, the pellet at the bottom of the tube, which contains the RNA, was removed and the supernatant discarded. The pellet was dissolved in 3.0 ml of solution D, 3.0 ml of isopropanol was added to the tube and the contents mixed well. After incubating the tube for 1 hour at −20° C., it was again spun in a centrifuge at 10,000×g for 10 minutes at 4° C. and the supernatant removed from the tube and discarded. (Note: Up to this point. the RNA had been protected from ribonucleases by the presence of guanidine isothiocyanate but was now no longer protected.) The pellet was washed with 75% (v/v) ethanol (DEPC-treated water (25%)) and the pellet was dried under vacuum for 2-3 minutes. The RNA pellet is re-suspended in 0.5-2 ml of DEPC-treated water.

Following the manufacturer's instructions, an Amersham Pharmacia Biotech first strand cDNA synthesis kit was employed to produce a single-stranded DNA copy of the 11-1F4 hybridoma mRNA using the Not I-d(T)$^{18}$ primer supplied with the kit. One reaction was performed for each of the two RNA samples isolated, as follows. The components used were: Bulk first strand cDNA reaction mix, Cloned FPLCpure™ Murine Reverse Transcriptase, RNAguard™, BSA, dATP, dCTP, dGTP, and dTTP, 200 mM DIT aqueous solution, Not I-d(T)$^{18}$ primer: 5'-d[AACTGGAAGAATTCGCGGCCGCAGGAA18]-3', and DEPC treated water.

Approximately 5 μg of total RNA in 20 μl DEPC water was heated to 65° C. for 10 min and then chilled on ice. The bulk first strand cDNA reaction mix was pipetted gently to obtain a uniform suspension and the reaction set up in a 0.5 ml microcentrifuge tube as below. 20 μl denatured RNA solution, 11 μl Bulk first strand cDNA reaction mix, 1 μl Not I-d(T)$^{18}$ primer, and 1 ul DTT solution for 33 μl total volume. The reactants were mixed gently by pipetting and incubated 37° C. for 1 hour.

The murine heavy and kappa light chain variable region genes ($V_H$ genes and $V_K$ genes, respectively) were then PCR amplified from the ssDNA template using the method described by Jones and Bendig (Bio/Technology 9:88).

Separate PCR reactions were prepared for each of the degenerate leader sequence specific primers (MHVI—MHV12 for $V_H$ and MKVI—MKV11 for $V_K$) with the appropriate constant region primer (an equimolar mix of MHCI—MHC3 for $V_H$ and MKC for $V_K$). Tables 1 & 2 detail the primers used to amplify the $V_H$ and $V_K$ region genes, respectively. In total, 12 heavy chain reactions and 11 kappa light chain reactions were performed. AmpliTaq® DNA polymerase was used to amplify the template cDNA in all cases, as follows.

The completed cDNA first strand synthesis reaction was heated at 90° C. for 5 minutes to denature the RNA-cDNA duplex and inactivate the reverse transcriptase and chilled on ice. Eleven GeneAmp™ PCR reaction tubes were labeled MKV1-11. For each tube a 100 μl reaction mixture was prepared, each reaction mixture containing 69.3 μl of sterile water, 10 μl of 10×PCR buffer II, 6 μl of 25 mM $MgCl_2$, 2 μl each of the 10 mM stock solutions of dNTPs, 2.5 μl of 10 mM MKC primer, 2.5 μl of one of the 10 mM MKV primers and 1 μl of RNA-cDNA template mix. To each of the tubes was then added 0.7 μl of AmpliTaq® DNA polymerase and the completed reaction mix overlaid with 50 μl of mineral oil.

A similar series of reaction mixes was prepared as described above to PCR-clone the mouse heavy chain variable region gene. However, this time twelve reaction tubes were labeled and one of the twelve MHV primers and the appropriate MHC primer were added to each. That is, to PCR-amplify the variable domain gene of a mouse γ1 heavy chain, for example, the MHC G1 primer was used.

The reaction tubes were loaded into a DNA thermal cycler and cycled (after an initial melt at 94° C. for 1.5 min) at 94° C. for 1 min, 50° C. for 1 min and 72° C. for 1 min over 25 cycles. The last cycle was followed by a final extension step at 72° C. for 10 min before cooling to 4° C. Except for between the annealing (50° C.) and extension (72° C.) steps when an extended ramp time of 2.5 min was used, a 30 sec ramp time was used between each step of the cycle. A 10 μl aliquot from each PCR reaction was run on a 1% (w/v) agarose/1× TBE buffer gel containing 0.5 μg/ml ethidium bromide to determine which of the leader primers produced a PCR-product. Positive PCR-clones were about 420-500 bp in size.

The above PCR-amplification process was repeated twice more and those PCR-reactions that appeared to amplify full-length variable domain gene were selected. A 6 μl aliquot of each potential PCR-product was directly cloned into the pCR™ II vector provided by the TA Cloning® kit, as described in the manufacturers instructions. Aliquots of 10.0% (v/v), 1.0% (v/v) and 0.1% (v/v) aliquots of the transformed E.coli cells were pipetted onto individual 90 mm diameter LB agar plates containing 50 μg/ml ampicillin, overlaid with 25 μl of the X-Gal stock solution and 40 μl of IPTG stock solution, and incubated overnight at 37° C. Positive colonies were identified by PCR-screening.

TABLE 1

PCR primers for cloning mouse kappa light chain variable region genes

| Name | Sequence (5'->3') | SEQ ID |
|---|---|---|
| MICV1 (30 mer) | ATGAAGATTGCCTGTTAGGCTGTTGGTGCTG | 1 |
| MKV2 (30 mer) | ATGGAGWCAGACACACTCCTGYTATGGGTG | 2 |
| MKV3 (30 mer) | ATGAGTGTGCTCACTCAGGTCCTGGSGTTG | 3 |
| MKV4 (33 mer) | ATGAGGRCCCCTGCTCAGWTTYTTGGMWTCTTG | 4 |
| MKV5 (30 mer) | ATGGATTTWCAGGTGCAGATTWTCAGCTTC | 5 |
| MKV6 (27 mer) | ATGAGGTKCYYTGYTSAYCTYCTCTGRGG | 6 |
| MKV7 (31 mer) | ATGGGCWTCAAAGATGGAGTCACAKWYYCWGG | 7 |

TABLE 1 -continued

PCR primers for cloning mouse kappa light chain variable region genes

| Name | Sequence (5'->3') | SEQ ID |
|---|---|---|
| MKV8 (25 mer) | ATGTGGGGAYCTKTTTYCMMTTTTTCAATG | 8 |
| MKV9 (25 mer) | ATGGTRTCCWCASCTCAGTTCCTTG | 9 |
| MKV10 (27 mer) | ATGTATATATGTTTGTTGTCTATTTCT | 10 |
| MKV11 (28 mer) | ATGGAAGCCCCAGCTCAGCTTCTCTTCC | 11 |
| MKC (20 mer) | ACTGGATGGTGGGAAGATGG | 12 |

TABLE 2

PCR primers for cloning mouse heavy chain variable region genes

| Name | Sequence (5'->3') | SEQ ID |
|---|---|---|
| MHVI (27 mer) | ATGAAATGCAGCTGGGGCATSTTCTTC | 13 |
| MHV2 (26 mer) | ATGGGATGGAGCTRTATCATSYTCTT | 14 |
| MHV3 (27 mer) | ATGAAGWTGTGGTTAAACTGGGTTTTT | 15 |
| MHV4 (25 mer) | ATGRACTTTGGGYTCAGCTTGRTTT | 16 |
| MHV5 (30 mer) | ATGGGACTCCAGGCTTCAATTTAGTTTTCCTT | 17 |
| MHV6 (27 mer) | ATGGCTTGTCYTTRGSGCTRCTCTTCTGC | 18 |
| MHV7 (26 mer) | ATGGRATGGAGCKGGRGTCTTTMTCTT | 19 |
| MHV8 (23 mer) | ATGAGAGTGCTGATTCTTTTGTG | 20 |
| MHV9 (30 mer) | ATGGMTTGGGTGTGGAMCTTGCTTATTCCTG | 21 |
| MHV10 (27 mer) | ATGGGCAGACTTACCATTCTCATTCCTG | 22 |
| MHV11 (28 mer) | ATGGATTTTGGGCTGATTTTTTTTATTG | 23 |
| MHV12 (27 mer) | ATGATGGTGTTAAGTCTTCTGTACCTG | 24 |
| MHCG1 (21 mer) | CAGTGGATAGACAGATGGGGG | 25 |
| MHCG2a (21 mer) | CAGTGGATAGACCGATGGGGG | 26 |
| MHCG2b (21 mer) | CAGTGGATGAGCTGATGGGGG | 27 |
| MHCG3 (21 mer) | CAAGGGATAGACAGATGGGGC | 28 |

Five μl aliquots from each PCR reaction were run on a 1% agarose/TBE (pH 8.8) gel to determine which had produced a PCR product of the correct size (ca. 450 bp). Those putative positive PCR products so identified were directly cloned into the pCR2.1 vector provided by the TA Cloning® kit and transformed into TOP10 competent cells as described in the manufacturer's protocol. Colonies containing the plasmid with a correctly sized insert were identified by PCR-screening the colonies using the 1212 and 1233 oligonucleotide primers (Table 3) according to the method of Güssow and Clackson (*Nucleic Acids Res.* 17:4000). Those putative positive clones so identified were double-stranded plasmid DNA sequenced using the ABI PRISM 310 Genetic Analyzer and the ABI PRISM BigDye™ terminator. Three positive clones each of the $V_H$ and $V_K$ genes from the B2C4 hybridoma cell line clone were sequenced, as were four positive clones of the $V_K$ gene and six of the $V_H$ gene from the B2D6 hybridoma cell line clone.

TABLE 3

Primers for PCR screening and sequencing transformed colonies.

| Name | Sequence (5'->3') | SEQ ID |
|---|---|---|
| 1212 (17 mer) | GTTTTCCCAGTCACGAC | 29 |
| 1233 (21 mer) | AGCGGATAATTTCACACAGGA | 30 |

The results of the 12 PCR reactions performed for each hybridoma clone (B2C4 and BCD6) to amplify the murine 11-1F4 heavy chain variable region gene are presented in Table 4(a).

The degenerate leader sequence primer MHV7, in combination with a mix of the MHCGI-3 constant region primers (Table 1), yielded a PCR product of about 600 bp from template cDNAs derived from both the B2C4 and B2D6 hybridoma cell lines. Since this band was larger than the expected size for an average $V_H$ gene (450 bp), it was not investigated further. Conversely, the degenerate leader sequence primer MHV6, in combination with a mix of the MHCGI-3 constant region primers (Table 1), yielded a PCR product of the expected size (450 bp) for a $V_H$ gene from template cDNA derived from both the B2C4 and B2D6 hybridoma cell lines.

TABLE 4

Results of the PCR amplifications performed to clone the murine 11-1F4 monoclonal antibody variable region heavy (a) and light (b) chain genes from the SP2/0 hybridoma cell lines B2C4 and B2D6. Column three contains a record of the actual PCR results. Where a band was observed for a particular combination of primers its size in base pairs (bp) was recorded in the appropriate space.

(a)

| | | Approximate Band Size (bp) | |
|---|---|---|---|
| $C_H$ Region Primer | Leader Primer | B2C4 | B2D6 |
| MHCG1-3 (mix) | MHV1 | | |
| " | MHV2 | | |
| " | MHV3 | | |
| " | MHV4 | | |
| " | MHV5 | | |
| " | MHV6 | 450 | 450 |
| " | MHV7 | 600 | 600 |
| " | MHV8 | | |
| " | MHV9 | | |
| " | MHV10 | | |
| " | MHV11 | | |
| " | MHV12 | | |

(b)

| | | Approximate Band Size (bp) | |
|---|---|---|---|
| $C_K$ Region Primer | Leader Primer | B2C4 | B2D6 |
| MKC | MKV1 | 450 | 450 |
| " | MKV2 | <450 | <450 |
| " | MKV3 | | |
| " | MKV4 | | |
| " | MKV5 | | |
| " | MKV6 | 200 | |
| " | MKV7 | | |
| " | MKV8 | | |
| " | MKV9 | | |
| " | MKV10 | | |
| " | MKV11 | | |

Sequence analysis of three clones from the B2C4 derived PCR product and five clones from the B2D6 derived PCR product revealed a single heavy chain variable region sequence (FIG. 2).

The cloning strategy used (amplification of the entire variable region gene by using primers which flank this region, i.e. leader sequence and constant region sequence specific primers) allowed the complete FR1 sequence to be identified. All eight clones sequenced had identical sequence in this region (FIG. 2).

The results of the 11 PCR reactions performed for each hybridoma clone (B2C4 and BCD6) to amplify the murine 11-1F4 kappa light chain variable region gene are presented in Table 4(b).

The degenerate leader sequence primer MKV6 in combination with the MKC constant region primer (Table 2), produced a PCR product of about 200 bp from template cDNA derived from the B2C4 hybridoma cell line only. Since this band was much smaller than the expected size for a $V_K$ gene (450 bp), it was not investigated further.

The degenerate leader sequence primer MKV2, in combination with the MKC constant region primer (Table 2), produced a PCR product which was smaller than the expected 450 bp band (when viewed on an agarose gel) from template cDNA derived from both the B2C4 and B2D6 hybridoma cell lines. In addition, previous $V_K$ cloning had found that the MKV2 primer amplified a well known kappa light chain pseudogene. Therefore, sequence analysis of one clone of each PCR product was performed in order to confirm that this product was a pseudogene and not the murine 11-1F4 $V_K$ gene. This sequence analysis revealed that this PCR clone was indeed the pseudogene.

Finally, the degenerate leader sequence primer MKV1, in combination with the MKC constant region primer (Table 1), produced a PCR product of about the expected size (450 bp) for a $V_K$ gene, from template cDNA derived from both the B2C4 and B2D6 hybridoma cell lines.

Sequence analysis of three clones of the B2C4 derived PCR product and four clones of the B2D6 derived PCR product revealed a single kappa light chain variable region sequence which could not be identified as a pseudogene.

Thus, the 11-1F4 heavy chain variable region gene was cloned (using constant region specific and leader sequence specific primers) from the hybridoma mRNA and sequenced.

When translated, the sequence gave a TVSS peptide sequence. Analysis of 122 rearranged human $V_H$ genes, recorded in the Kabat database (Kabat et al.—*Sequences of Proteins of Immunological Interest*), revealed that 84% of these sequences had a TVSS peptide sequence. It was therefore concluded that the $V_H$ gene isolated was the correct 11-1F4 gene sequence.

The murine 11-1F4 variable region kappa light chain gene was also successfully cloned and sequenced, as was a non-functional $V_K$ pseudogene gene. This pseudogene was first identified by Carroll et al (*Molecular Immunology* (1988) 25:991). The sequence arises from an aberrent mRNA transcript which is present in all standard fusion partners derived from the original MOPC-21 tumor (including SP2/0). As a result of the aberrant mRNA, the invariant cysteine at position 23 is replaced by a tyrosine residue, and the VJ joint is out of frame, resulting in a stop codon at position 105.

It is common for lymphoid or hybridoma cells to synthesize more than one rearranged light immunoglobulin mRNA. These mRNAs are usually non productive due to the presence of termination codons or frame shifts not usually seen in functional $V_K$ genes. These pseudo messengers often present major problems when cloning immunoglobulin genes from hybridomas because they are very good substrates for V region PCR, despite the fact that they do not encode functional polypeptides.

The 11-1F4 $V_K$ gene sequence was identified after detailed sequence analysis of seven separate PCR clones, isolated from two different PCR products to yield SEQ. ID NO: 36. Since all sequences were identical, it was accepted as the correct 11-1F4 kappa light chain variable region sequence.

The cloned $V_H$ and $V_K$ region genes were used to make the chimeric mouse-human 11-1F4 monoclonal antibody, which was then be analyzed to confirm specific binding to AL fibrils.

EXAMPLE 2

Construction of chimeric mouse-human 11-1F4 (c11-1F4) antibody

In order to allow transient expression of the 11-1F4 $V_H$ and $V_K$ variable region genes described above in mammalian cells as part of a chimeric mouse -human antibody, it was necessary to modify the 5'- and 3'-ends using specifically designed PCR primers (Table 5). The oligonucleotide primers F39836 and F39837 were used to PCR modify the 11-1F4 $V_K$ gene, while primers F39835 and F58933 were used to PCR modify the 11-1F4 $V_H$ gene. The back (BAK) primers F39836 and F39835 introduced a HindIII restriction site, a Kozak translation initiation site, and an immunoglobulin leader sequence to the 5' ends of the $V_K$ and $V_H$ genes respectively. The forward (FOR) oligonucleotide primer F39837 introduced a splice donor site and a BamHI restriction site to the 3' end of the $V_K$ gene while the forward (FOR) oligonucleotide primer F58933 appended the first 22 base pairs of the gamma-1$CH_1$ gene including an ApaI restriction site to the 3' end of the $V_H$ gene.

TABLE 5

Oligonucleotide primers used to PCR modify the 11-1F4 heavy and kappa light chain variable region genes.

| Name | Sequence 5'->3' | SEQ ID NO: |
|---|---|---|
| F39835 VH BAK | AAGCTTGCCGCCACCATGGCTGTCCTGGGGCTGCT CITCTGC | 31 |
| F58933 VH FOR | CCGATGGGCCCTTGGTGGAGGCTGAGGAGACGGTG ACTGAGGTTCC | 32 |
| F39836 YK BAK | AAGCTTGCCGCCACCATGAAGTTGCCTGTTAGGCT GTTGGTGC | 33 |
| F39837 VK FOR | GGATCCACTCACGTTTGATTTCCAGCTTGGTCCCC CCTCCGA | 34 |

The Kozak consensus sequence is crucial to the efficient translation of a variable region sequence (Kozak—*J Mol Bio* 196:947). It defines the correct AUG codon from which a ribosome commences translation, and the single most critical base is the adenine (or less preferably, a guanine) at position −3, upstream of the AUG start.

The immunoglobulin leader sequence ensures that the expressed antibody is secreted into the medium and therefore is easily harvested and purified. The leader sequences used in this instance were the murine 11-1F4 $V_K$ and $V_H$ leader sequences cloned from the hybridoma cDNA during the $V_H$ and $V_K$ cloning process.

The splice donor sequence is important for the correct in-frame attachment of the light chain variable region to its appropriate constant region, thus splicing out the 130 bp $V_K$:$C_K$ intron. The heavy chain variable region was attached directly to its appropriate constant region gene via the ApaI site, thus eliminating the need for a splice donor site.

The sub-cloning restriction sites HindIII and BamHI, and HindIII and ApaI, respectively, bracket the modified $V_K$ and $V_H$ variable region genes, while the use of different unique restriction sites ensured directional sub-cloning into the appropriate mammalian expression vector.

The 11-1F4 light chain variable region gene was first carefully analyzed to identify any unwanted splice donor sites, splice acceptor sites, and Kozak sequences (see Table 6). Both the heavy and light chain variable region genes were analyzed for the presence of any extra sub-cloning restriction sites which would later interfere with the sub-cloning and/or expression of functional whole antibody. None were found.

TABLE 6

Sequences important for the efficient expression of immunoglobulin genes in mammalian cells.

| Name | Consensus DNA Sequences |
|---|---|
| Kozak translation initiation site | CCGCCRCC**AUGG** |
| Kappa light chain splice donor site | AC::**GT**RAGT |
| Heavy chain splice donor site | AG::**GT**RAGT |
| Immunoglobulin splice acceptor site | YYYYYYYYYYNC**AG**::G |

Bases shown in bold are considered to be invariant within each consensus sequence.

Separate PCR reactions were prepared as follows, one for each variable region gene. The plasmids 11-1F4 $V_H$.pCR2.1 and 11-1F4 $V_K$.pCR2.1 described above were used as templates. A 100 μl reaction mixture was prepared in each PCR tube, each mixture containing up to 41 μl of sterile water, 10 μl of 10×PCR buffer I, 8 μl of the 10 mM stock solution of dNTPs, 1 μl of 10 mM of 5' forward primer, 1 μl of the 10 mM 3' Reverse primer, and 1 μl of a 1/10 dilution of template DNA. Finally, 0.5 μl of AmpliTaq® DNA polymerase (2.5 units) was added before overlaying the completed reaction mixture with 50 μl of mineral oil. The reaction tubes were loaded into a DNA thermal cycler and cycled (after an initial melt at 94° C. for 1 min) at 94° C. for 30 sec, 68° C. for 30 sec and 72° C. for 50 sec over 25 cycles. The completion of the last cycle was followed with a final extension step at 72° C. for 7 min before cooling to 4° C. A 10 μl aliquot from each PCR reaction tube was run on a 1.2% (w/v) agarose/1× TBE buffer gel containing 0.5 μg/ml ethidium bromide to determine size and presence of a PCR-product. Positive PCR-clones were about 420 bp in size. Those putative positive PCR products so identified were directly cloned into the pCR2.1 vector, provided by the Topo TA Cloning® kit, and transformed into TOP10 competent cells as described in the manufacturer's protocol. Colonies containing the plasmid with a correctly sized insert were identified by PCR-screening the colonies using the 1212 and 1233 oligonucleotide primers (Table 3) according to the method of Güssow and Clackson. Those putative positive clones so identified were double-stranded plasmid DNA sequenced using the ABI PRISM 310 Genetic Analyzer and the ABI PRISM BigDye™ terminator. Two positive clones each of the Topo TA cloned $V_H$ and $V_K$ genes were sequenced.

Figure 4:
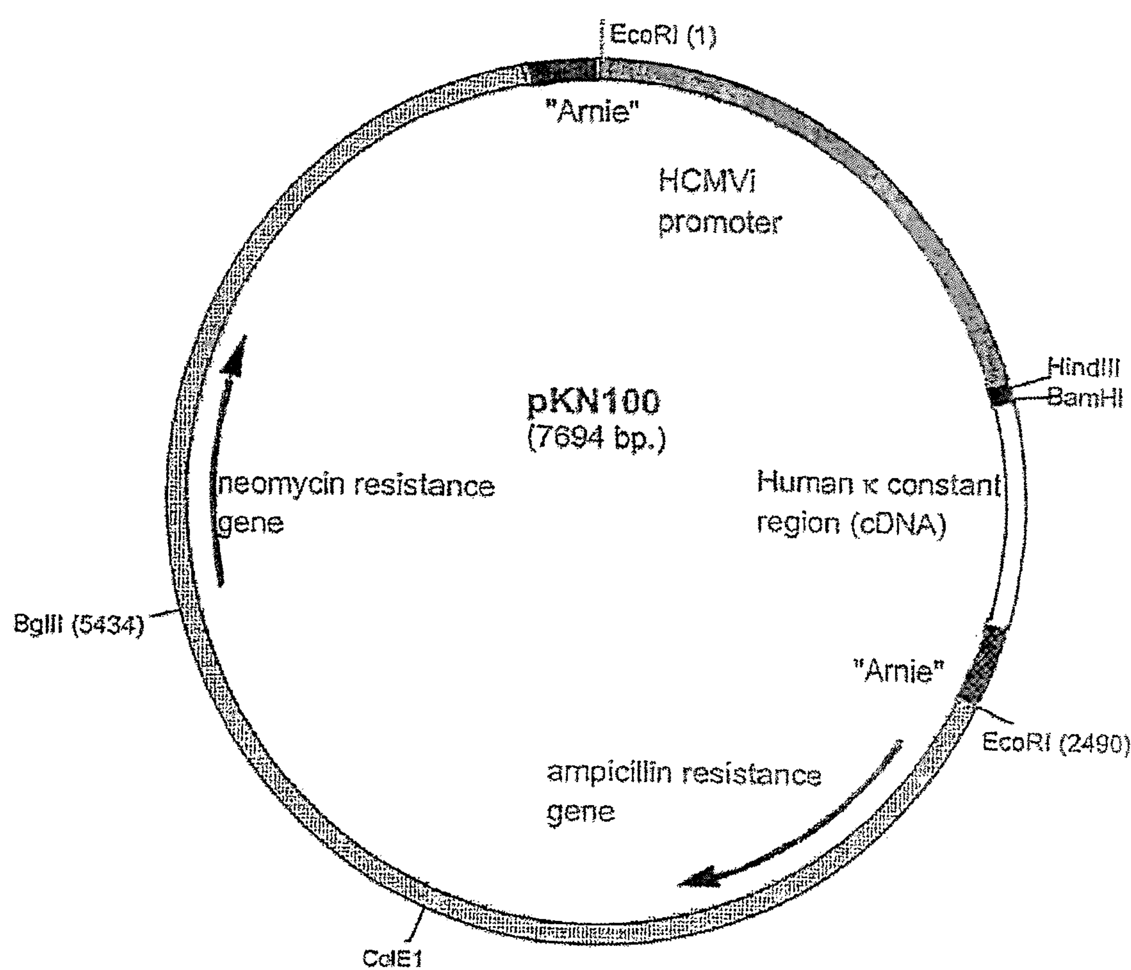
FIG. 4 is a map of the immunoglobulin kappa light chain expression vector pKN100. It consists of a pSV2 vector fragment, which has the SV40 early and crippled SV40 late promoter, the SV40 origin and the Co1E1 origin. It also has the ampicillin resistance and neo genes. The crippled SV40 late promoter drives the neo genes. It also has the HCMVi promoter, a multiple cloning site (containing the BamHI and HindIII restriction sites) for the insertion of an immunoglobulin variable region gene, and cDNA for the human kappa constant region gene terminated by a spaC2 termination signal sequence ("Arnie"), which is in the same orientation as the kappa light chain expression cassette.

Clones containing the correctly modified 11-1F4 $V_H$ and 11-1F4 $V_K$ genes were identified and the modified V genes from these clones were subcloned into their respective expression vectors to facilitate the expression of chimeric heavy and kappa light chains in mammalian cells. The modified 11-1F4 $V_K$ gene was subcloned into the expression vector pKN100 (FIG. 4) as a HindIII-BamHI fragment; this vector contains a human kappa constant region gene (allotype: Km (3 Ala153, Ser191)). The modified 11-1F4 $V_H$ gene was also subcloned as a HindIII-ApaI fragment into the expression vector pG1D200 (FIG. 5); this vector contained a human γ1 constant region gene (allotype: G1m (−1 Glu377, Met38I, −2 Ala462, 3 Arg222, Ser229)). Both the kappa and γ1 constant region allotypes used are commonly found in the caucasian population. The ligated expression constructs, 11-1F4VK.pKN100 and 11- 1F4VH.pG1D200, were then used to transform DH5a competent cells, and positive clones were identified using the PCR screening method discussed above with the original PCR modification primers (Table 4). The expression vectors are readily available.

EXAMPLE 3

Construction of a single supervector for transient expression of chimeric 11-1F4 in COS Cells.

A single supervector expressing both immunoglobulin chains of the chimeric 11-1F4 antibody was constructed as follows. The 11-1F4 kappa light chain expression cassette (which contained the HCMVi promoter, the 11-1F4 kappa light chain variable region gene, and the kappa light chain constant region gene) was restriction enzyme digested (EcoRI at positions 1 and 2490) out of the 11-1F4VK.pKN100 construct (FIG. 4) and subsequently ligated into the 11-1F4VHpG1D200 construct via the unique EcoRl (position 4297, FIG. 5). This ligation resulted in the construction of a supervector construct, pG1KD200-11-1F4, containing both the heavy and kappa light chains of the 11-1F4 chimeric antibody.

EXAMPLE 4

Transient Expression of the Chimeric γ1/κ.11-IF4 Whole Antibody in COS Cells

The chimeric 11-IF4 antibody was transiently expressed in COS cells from the European Collection of Cell Cultures (ECACC) in two ways:

(i) By cotransfection of 10 μg of each of the vector constructs 11-1 F4VK.pKN 100 and 11-1F4VH.pG1D200. Co-transfections were carried out in duplicate.

(ii) By transfection of 13 μg of the single supervector construct pG1KD200-11-1F4. Supervector transfections were carried out five times.

The following transfection method was used. The COS cell line was grown in DMEM supplemented with 10% (v/v) FCS, 580 μg/ml L-glutamine and 50 Units/ml penicillin/50 μg/ml streptomycin ("media") in a 150 $cm^2$ flask until confluent. The cells were trypsinized, spun down in a bench top centrifuge (250 g for 5 min), then re-suspended in 6 ml of media before dividing them equally between three 150 $cm^2$ flasks, each containing 25 ml of fresh, pre-warmed media. The cells were incubated overnight at 37° C. in 5% $CO_2$ and then harvested the next day while they are still growing exponentially. Each flask contained approximately $1\times10^7$ cells. The cells were trypsinized again, pelleted as before, and washed in 20 ml of PBS, following which they were re-suspend in sufficient PBS to create a cell concentration of $1\times10^7$ cells/ml. 700 μl of these washed COS cells were pipetted into a Gene Pulser® cuvette, to which was then added 1 μl of both the heavy chain and kappa light chain expression vector DNA (each at 10 μg) or 13 μg of the super-vector construct. A 1900 Volt, 25 μFarad capacitance pulse was delivered to the mixture using the Bio-Rad Gene Pulser® apparatus. The pulsing was repeated for each experimental transfection and a "no DNA" control (in which the COS cells were electroporated in the absence of any DNA). A positive control of a previously-expressed antibody was also carried out to test the efficiency of the COS cells.

The COS cells were allowed to recover at room temperature for 10 min, then gently pipetted the into a 10 cm diameter tissue culture dish containing 8 ml of pre-warmed DMEM supplemented with 10% (v/v) γ-globulin free FBS, 580 μg/ml L-glutamine and 50 Units/ml penicillin/50 μg/ml streptomycin, and incubated in 5% $CO_2$ at 37° C. for 72 hours before harvesting the COS cell supernatant for analysis. After incubation for 72 hours the medium was collected, spun to remove cell debris and analyzed by ELISA for chimeric antibody production and antigen binding of the c11-1F4 antibody.

EXAMPLE 5

Quantification of the Chimeric γ1/κ11-1F4 Antibody Via Capture ELISA

Following expression, the whole IgG molecules present in the COS cell supernatant were quantified using a capture ELISA assay. IgG molecules were captured on a Nunc-Immuno MaxiSorb™ plate via an immobilized goat anti-human IgG, Fcγ fragment—specific antibody, and detected via an anti-human kappa light chain peroxidase conjugated antibody. A standard curve was generated by capturing and detecting known concentrations of a standard IgG antibody on the same plate in the same way as follows. Each well of a 96-well immunoplate was coated with 100 μl aliquots of 0.4 μg/ml goat anti-human IgG antibody diluted in PBS and incubated overnight at 4° C. The excess coating solution was removed and the plate was washed three times with 200 μl/well of washing buffer (1×PBS, 0.1% TWEEN). Into all wells except the wells in column 2, rows B to G, was dispensed 100 μl of SEC buffer. A 1 μg/ml solution of the human IgG1/kappa antibody in SEC buffer was prepared to serve as a standard and 200 μl/well was pipetted into the wells in column 2, rows B and C. The medium from the transfected cos cells was centrifuged (250 g, 5 min), saving the supernatant. An aliquot of 200 μl of the supernatant from the "no DNA" control (in which COS cells were transfected in the absence of DNA) was pipetted into the well in column 2, row D, and aliquots of 200 μl/well of experimental supernatants were pipetted into the wells in column 2, rows E, F, and G. The 200 μl aliquots in the wells of column 2, rows B to G were mixed and then 100 μl was transferred from each well to the neighboring well in column 3. This process was continued to column 11 with a series of 2-fold dilutions of the standard, control, and experimental samples, following which all were incubated at 37° C. for 1 hour and all the wells were rinsed six times with 200 μl aliquots of washing buffer. The goat anti-human kappa light chain peroxidase conjugate was diluted 5000-fold in SEC buffer and 100 μl of the diluted conjugate added to each well, followed by a repetition of the incubation and rinsing steps. To each well was added 150μl of K-BLUE substrate, followed by incubation in the dark at 25° C. for 10min. The reaction was stopped by adding 50 μl of RED STOP solution to each well and the optical density was read at 655 nm.

EXAMPLE 6

Binding Analysis of the Chimeric 11-1F4 Antibody

The chimeric 11-1F4 antibody was tested for binding to amyloid fibrils using a direct binding ELISA assay. Synthetic fibrils were formed from an immunoglobulin light chain protein and used to monitor the reactivity of the antibody in a solid-state ELISA-based assay using a "low-binding" polystyrene plates (Costar, #3474). Immediately prior to coating the plate, a mass of 250 μg of fibrils was diluted to 1 ml with coating buffer (0.1% bovine serum albumin in phosphate buffered saline pH 7.5). The sample was then sonicated for 20 sec using a Tekmar Sonic Disruptor sonicating probe, with the power set to 40% of maximum, resulting in a solution of short fibrils composed of up to 2-5 protofiliments each. This solution was then diluted to 5 ml, mixed well by vortex, and aliquoted into the wells of the plate. This process yielded 50 μl of fibril solution having a concentration of 50 μg/ml in each well. The plate was then dried overnight by placing it uncovered in a 37° C. incubator.

The ELISA assay was then performed as follows within 48 hours of preparing the plate. The wells were blocked by the addition of 100 μl of 1% BSA in PBS and incubated for 1 hour at room temperature on a shaker. The plate was washed ×3 in PBS, 0.05% Tween 20 (v/v). To each well of the plate was added 50 μl of a solution of c11-1F4 (3 μg/ml antibody in 0.1% BSA/PBS) and the plate incubated at room temperature for 1 hour on a shaker. The plate was again washed ×3 (as before) and detection of bound antibody was accomplished using a biotinylated goat anti-mouse IgG antibody (Sigma# B-8774, anti-heavy and light-chain).

Results

Sequence analysis of the successfully modified $V_H$ and $V_K$ genes revealed the correct sequence was present. Detailed DNA and amino acid sequences of the modified 11-1F4 $V_K$ and $V_H$ genes are presented in FIGS. 3 & 4. The modified $V_K$ and $V_H$ genes were successfully cloned into the mammalian expression vectors pG1D200 and pKN100 respectively, and the resulting 11-1F4VK.pKN100 and 11-1F4VHpG1D200 constructs were used for cotransfection of mammalian cells.

The 11-1F4VK.pKN100 and 11-1F4VHpG1D200 constructs were also subsequently used to construct a single supervector (pG1KD200-11-1F4), which expressed the chimeric 11-1F4 antibody in mammalian cells. The chimeric II-1F4 antibody expression levels, from both cotransfections and supervector transfections of ECACC COS cells were assayed. The expression levels observed from the pG1KD200-11-1F4 supervector transfections (10326 ng/ml) were 3.7 fold higher than the levels observed from the corresponding co-transfections of the 11-1F4VK.pKN100 and 11-1F4VHpG1D200 constructs (2820 ng/ml).

Figure 8:
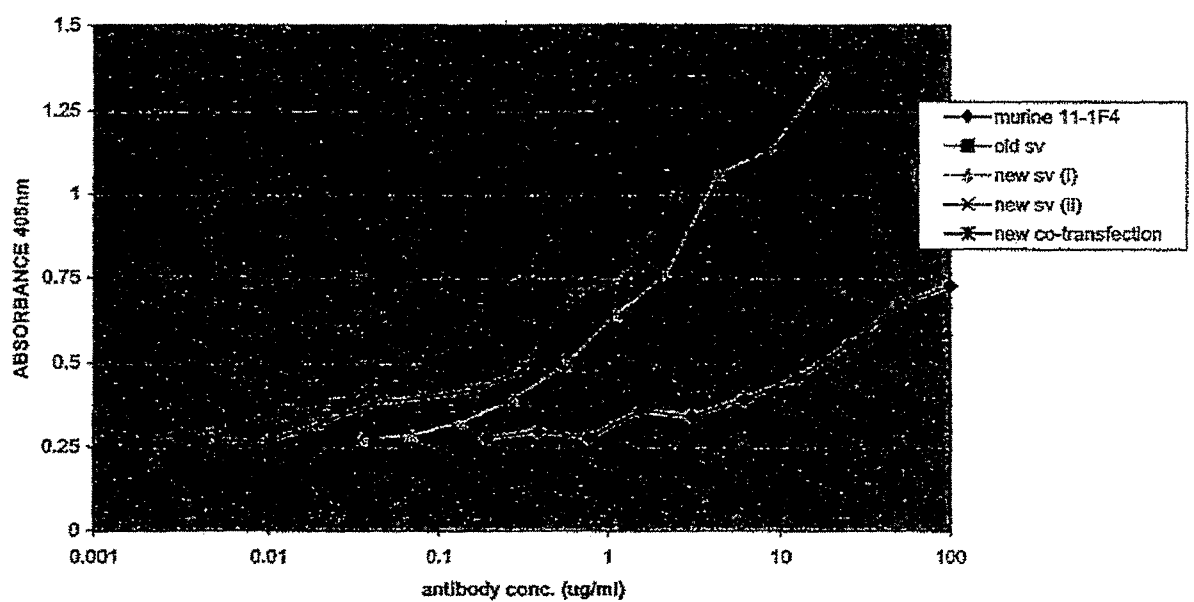
FIG. 8 is a graphical representation of the result of the amyloid fibril binding ELISA assay. The cos cell supernatants containing chimeric 11-1F4 antibody were tested separately on the same ELISA plate along with purified murine 11-1F4 antibody. The absorbance was read at OD405.

Following expression and quantification, the chimeric 11-1F4 antibody was tested for binding to target antigen (amyloid fibrils kindly supplied by the NCI) by direct binding ELISA. The results of the binding ELISA are presented in FIG. 8. Supenatants from the two best individual pG1KD200-11-1F4 supervector transfections were assayed in parallel with one supernatant from the corresponding co-transfection.

The results indicated that the chimeric 11-1F4 antibody bound to the amyloid fibrils with a higher affinity than its murine equivalent. This result is surprising and unexpected because normally a chimeric antibody would be expected to have a binding affinity comparable to the original murine antibody. Without intending to be bound by the particular mechanism, the inventors believe it is possible that the net effect of combining the 11-1F4 murine V regions with the human γ1/κ C regions used to create the chimeric 11-1F4 antibody produced an antibody of higher affinity.

In the description and claims of this specification the word "comprise" and variations of that word, such as "comprises" and "comprising" are not intended to exclude other features, additives, components, integers or stepsbut rather, unless otherwise stated explicitly, the scope of these words should be construed broadly such that they have an inclusive meaning rather than an exclusive one.

Although the compositions and methods of the invention have been described in the present disclosure by way of illustrative examples, it is to be understood that the invention is not limited thereto and that variations can be made as known by those skilled in the art without departing from the teachings of the invention defined by the appended claims.

What is claimed is:

1. A chimeric mouse-human antibody for treating primary amyloidosis comprising a VK and VH region, wherein the VK region is SEQ ID NO: 47 and the VH region is SEQ ID NO: 48, wherein the chimeric antibody binds to amyloid fibrils with a higher affinity than its murine equivalent.

2. The chimeric mouse-human antibody of claim 1 which binds to an epitope expressed by the β-pleated sheet configuration of amyloid fibrils with higher affinity than the mouse antibody comprising the VK region of SEQ ID NO: 36 and the VH region of SEQ ID NO: 35.

3. A pharmaceutical composition comprising the antibody of claim 1 and a pharmaceutically acceptable carrier.

4. A method of treating an amyloid deposition disease in a human patient in need of such treatment which comprises administering to the patient the antibody of claim 1 together with a pharmaceutically acceptable carrier, in an amount effective to treat said amyloid deposition disease.

5. The method of claim 4 wherein the amyloid deposition disease is primary amyloidosis.

6. A method of detecting the presence of amyloid deposits in a patient suspected of having such deposits which comprises administering to the patient an amount of the antibody of claim 1 having a detectable label attached thereto, the amount of antibody administered being sufficient to allow detection of amyloid deposits if such are present.

7. The method of claim 6 wherein the detectable label is 1241.

8. A polypeptide selected from SEQ. ID NO: 47 and SEQ. ID NO: 48.

* * * * *

UNITED STATES PATENT AND TRADEMARK OFFICE

CERTIFICATE OF CORRECTION

PATENT NO. : 11,530,257 B2
APPLICATION NO. : 16/626613
DATED : December 20, 2022
INVENTOR(S) : Tarran Jones, Alison Levy and Siobhan O'Brien It is certified that error appears in the above-identified patent and that said Letters Patent is hereby corrected as shown below:

On the Title Page

Please delete the Title page and insert the Title Page shown on the attached Title page.

In the Claims

Column 35, Lines 5-6, in Claim 1, delete ", wherein the chimeric antibody binds to amyloid fibrils with a higher affinity than its murine equivalent".

Column 35, Line 28, in Claim 7, replace "1241" with --$^{124}$I--.

Column 35, after Line 30, insert the claims:
--9. The antibody of claim 1, wherein the antibody has a detectable label.
10. The antibody of claim 9, wherein the label is a radiolabel.
11. The antibody of claim 10, wherein the label is $^{124}$I.--.

Signed and Sealed this
Twenty-first Day of March, 2023

Katherine Kelly Vidal

Katherine Kelly Vidal
*Director of the United States Patent and Trademark Office*

(12) United States Patent
Jones et al.

(10) Patent No.: US 11,530,257 B2
(45) **Date of Patent: *Dec. 20, 2022**

(54) CHIMERIC ANTIBODIES FOR TREATMENT OF AMYLOID DEPOSITION DISEASES

(71) Applicant: The Trustees of Columbia University in the City of New York, New York, NY (US)

(72) Inventors: Tarran Jones, Radlett (GB); Alison Levy, Harpenden (GB); Siobhan O'Brien, Bishops Stortford (GB)

( * ) Notice: Subject to any disclaimer, the term of this patent is extended or adjusted under 35 U.S.C. 154(b) by 120 days.

This patent is subject to a terminal disclaimer.

(21) Appl. No.: 16/626,613

(22) PCT Filed: Jun. 28, 2018

(86) PCT No.: PCT/US2018/039905

§ 371 (c)(1),
(2) Date: Dec. 26, 2019

(87) PCT Pub. No.: WO2019/006062

PCT Pub. Date: Jan. 3, 2019

(65) Prior Publication Data

US 2020/0181246 A1 Jun. 11, 2020

Related U.S. Application Data

(60) Provisional application No. 62/526,835, filed on Jun. 29, 2017.

(51) Int. Cl.

*C07K 16/18* (2006.01)
*A61K 38/00* (2006.01)
*C12N 15/86* (2006.01)

(52) U.S. Cl.

CPC .............. *C07K 16/18* (2013.01); *C12N 15/86* (2013.01); *A61K 38/00* (2013.01); *C07K 2317/24* (2013.01); *C07K 2317/34* (2013.01)

(58) Field of Classification Search

CPC ........................... C07K 16/18; C07K 2317/24; C07K 2317/34; A61K 38/00

See application file for complete search history.

(56) References Cited

U.S. PATENT DOCUMENTS

| | | | |
|---|---|---|---|
| 7,256,273 | B2 | 8/2007 | Basi et al. |
| 7,927,594 | B2 | 4/2011 | Rosenthal et al. |
| 8,105,594 | B2 | 1/2012 | Solomon et al. |
| 8,195,594 | B1 | 6/2012 | Bryce |
| 8,404,815 | B2 | 3/2013 | Schenk et al. |
| 8,591,894 | B2 | 11/2013 | Holzman et al. |
| 2009/0297439 | A1 | 12/2009 | Comoglio et al. |
| 2010/0150906 | A1 | 6/2010 | Pfeifer et al. |
| 2011/0177066 | A1 | 7/2011 | Schenk |
| 2013/0295082 | A1 | 11/2013 | Garidel et al. |
| 2016/0024197 | A1 | 1/2016 | Burbidge et al. |
| 2016/0243230 | A1 | 8/2016 | Wall et al. |

FOREIGN PATENT DOCUMENTS

| | | | |
|---|---|---|---|
| EA | 010902 | B1 | 12/2008 |
| EA | 015654 | B1 | 10/2011 |
| EP | 2730659 | A2 | 5/2014 |
| JP | 2009-530374 | A | 8/2009 |
| JP | 2017528449 | A | 9/2017 |
| RU | 2475500 | C2 | 2/2013 |
| RU | 2498999 | C2 | 11/2013 |
| WO | 9960024 | A1 | 11/1999 |
| WO | 1999060024 | A1 | 11/1999 |
| WO | 2003077858 | A2 | 9/2003 |
| WO | 2007108756 | A1 | 9/2007 |
| WO | 2007113172 | A2 | 10/2007 |
| WO | 2008011348 | A2 | 1/2008 |
| WO | 2016032949 | A1 | 3/2016 |
| WO | 2016187546 | A1 | 11/2016 |

OTHER PUBLICATIONS

The Extended European Search Report dated Mar. 11, 2021 for corresponding EP Application No. 18822805.0.

Langer AL et al. Results of phase 1 study of chimeric fibril-reactive monoclonal antibody 11-1 F4 in patients with AL amyloidosis. Blood, 2015, 126(23), 188, Meeting abstract 653. (Year: 2015).

Japanese Office Action for corresponding Japanese Application No. 2020-505320 dated Apr. 27, 2021.

Van Doren et al. Nonchemotherapy treatment of immunoglobulin light chain amyloidosis. Acta Haematol. 2020, 143:373-380. (Year:2020).

Extended European Search Report dated Apr. 23, 2021 for corresponding European Application No. 18 840 642.5.

Comenzo RL et al. Managing systemic light-chain amyloidosis. J. National Comprehensive Cancer Network, 2007, 5, 179-187. (Year: 2007).

Lin CY et al. Toxic human islet amyloid polypeptide (h-IAPP) oligomers are intracellular, and vaccination to induce anti-toxic oligomer antibodies does not prevent h-IAPP-induced beta-cell apoptosis in h-IAPP transgenic mice. Diabetes, 2007, 56, 1324-1332. (Year: 2007).

Lentzsch, Suzanne. Phase Ia/I b study of 11-1 F4 mAb for the treatment of AL amyloidosis, 2015 NIH Grant# 1 RO 1 FD005110-01, retrieved from Grantome.com on Dec. 9, 2019. (Year: 2019).

Guidance for Industry: Estimating the maximum safe starting dose in initial clinical trials for therapeutics in adult healthy volunteers. US Dept. of Health and Human Service, Food and Drug Administration (FDA), Center for Drug Evaluation and Research (CDER). Jul. 2005, 30 pages. (Year: 2005).

(Continued)

*Primary Examiner* — Gregory S Emch

(74) *Attorney, Agent, or Firm* — McCormick, Paulding & Huber PLLC

(57) ABSTRACT

A chimeric mouse-human antibody for treatment of amyloid deposition diseases, pharmaceutical compositions comprising the antibody, methods and materials for producing the antibody, and methods for treating an amyloid deposition disease using the antibody and the pharmaceutical composition.

11 Claims, 8 Drawing Sheets

Specification includes a Sequence Listing.

SEQUENCE LISTING

```
<160> NUMBER OF SEQ ID NOS: 48

<210> SEQ ID NO 1
<211> LENGTH: 31
<212> TYPE: DNA
<213> ORGANISM: Mus musculus

<400> SEQUENCE: 1

atgaagattg cctgttaggc tgttggtgct g                                    31


<210> SEQ ID NO 2
<211> LENGTH: 31
<212> TYPE: DNA
<213> ORGANISM: Mus musculus

<400> SEQUENCE: 2

atggagwcag acacactccc tgytatgggt g                                    31


<210> SEQ ID NO 3
<211> LENGTH: 30
<212> TYPE: DNA
<213> ORGANISM: Mus musculus

<400> SEQUENCE: 3

atgagtgtgc tcactcaggt cctggsgttg                                      30


<210> SEQ ID NO 4
<211> LENGTH: 33
<212> TYPE: DNA
<213> ORGANISM: Mus musculus

<400> SEQUENCE: 4

atgaggrccc ctgctcagwt tyttggmwtc ttg                                  33


<210> SEQ ID NO 5
<211> LENGTH: 30
<212> TYPE: DNA
<213> ORGANISM: Mus musculus

<400> SEQUENCE: 5

atggatttwc aggtgcagat twtcagcttc                                      30


<210> SEQ ID NO 6
<211> LENGTH: 29
<212> TYPE: DNA
<213> ORGANISM: mus musculus

<400> SEQUENCE: 6

atgaggtkcy ytgytsayct yctctgrgg                                       29
```

<210> SEQ ID NO 7
<211> LENGTH: 32
<212> TYPE: DNA
<213> ORGANISM: Mus musculus

<400> SEQUENCE: 7
atgggcwtca aagatggagt cacakwyycw gg 32

<210> SEQ ID NO 8
<211> LENGTH: 31
<212> TYPE: DNA
<213> ORGANISM: Mus musculus

<400> SEQUENCE: 8
atgtggggay ctkttttycm mtttttcaat g 31

<210> SEQ ID NO 9
<211> LENGTH: 25
<212> TYPE: DNA
<213> ORGANISM: Mus musculus

<400> SEQUENCE: 9
atggtrtccw casctcagtt ccttg 25

<210> SEQ ID NO 10
<211> LENGTH: 27
<212> TYPE: DNA
<213> ORGANISM: Mus musculus

<400> SEQUENCE: 10
atgtatatat gtttgttgtc tatttct 27

<210> SEQ ID NO 11
<211> LENGTH: 28
<212> TYPE: DNA
<213> ORGANISM: Mus musculus

<400> SEQUENCE: 11
atggaagccc cagctcagct tctcttcc 28

<210> SEQ ID NO 12
<211> LENGTH: 20
<212> TYPE: DNA
<213> ORGANISM: Mus musculus

<400> SEQUENCE: 12
actggatggt gggaagatgg 20

<210> SEQ ID NO 13
<211> LENGTH: 27
<212> TYPE: DNA
<213> ORGANISM: Mus musculus

<400> SEQUENCE: 13
atgaaatgca gctggggcat sttcttc 27

<210> SEQ ID NO 14
<211> LENGTH: 26
<212> TYPE: DNA
<213> ORGANISM: Mus musculus

<400> SEQUENCE: 14
atgggatgga gctrtatcat sytctt 26

<210> SEQ ID NO 15
<211> LENGTH: 27
<212> TYPE: DNA
<213> ORGANISM: Mus musculus

<400> SEQUENCE: 15
atgaagwtgt ggttaaactg ggttttt 27

<210> SEQ ID NO 16
<211> LENGTH: 25
<212> TYPE: DNA
<213> ORGANISM: Mus musculus

<400> SEQUENCE: 16
atgractttg ggytcagctt grttt 25

<210> SEQ ID NO 17
<211> LENGTH: 32
<212> TYPE: DNA
<213> ORGANISM: Mus musculus

<400> SEQUENCE: 17
atgggactcc aggcttcaat ttagttttcc tt 32

<210> SEQ ID NO 18
<211> LENGTH: 29
<212> TYPE: DNA
<213> ORGANISM: Mus musculus

<400> SEQUENCE: 18
atggcttgtc yttrgsgctr ctcttctgc 29

<210> SEQ ID NO 19
<211> LENGTH: 27
<212> TYPE: DNA
<213> ORGANISM: Mus musculus

<400> SEQUENCE: 19
atggratgga gckggrgtct ttmtctt 27

<210> SEQ ID NO 20
<211> LENGTH: 23
<212> TYPE: DNA
<213> ORGANISM: Mus musculus

<400> SEQUENCE: 20
atgagagtgc tgattctttt gtc 23

<210> SEQ ID NO 21
<211> LENGTH: 31
<212> TYPE: DNA
<213> ORGANISM: Mus musculus

<400> SEQUENCE: 21
atggmttggg tgtggamctt gcttattcct g 31

<210> SEQ ID NO 22
<211> LENGTH: 28
<212> TYPE: DNA
<213> ORGANISM: Mus musculus

<400> SEQUENCE: 22
atgggcagac ttaccattct cattcctg 28

<210> SEQ ID NO 23
<211> LENGTH: 28
<212> TYPE: DNA
<213> ORGANISM: Mus musculus

<400> SEQUENCE: 23
atggattttg ggctgatttt ttttattg 28

<210> SEQ ID NO 24
<211> LENGTH: 27
<212> TYPE: DNA
<213> ORGANISM: Mus musculus

<400> SEQUENCE: 24
atgatggtgt taagtcttct gtacctg 27

<210> SEQ ID NO 25
<211> LENGTH: 21
<212> TYPE: DNA
<213> ORGANISM: Mus musculus

<400> SEQUENCE: 25
cagtggatag acagatgggg g 21

<210> SEQ ID NO 26
<211> LENGTH: 21
<212> TYPE: DNA
<213> ORGANISM: Mus musculus

<400> SEQUENCE: 26
cagtggatag accgatgggg g 21

<210> SEQ ID NO 27
<211> LENGTH: 21
<212> TYPE: DNA
<213> ORGANISM: Mus musculus

<400> SEQUENCE: 27
cagtggatga gctgatgggg g 21

<210> SEQ ID NO 28
<211> LENGTH: 21
<212> TYPE: DNA
<213> ORGANISM: Mus musculus

<400> SEQUENCE: 28
caagggatag acagatgggg c 21

<210> SEQ ID NO 29
<211> LENGTH: 17
<212> TYPE: DNA
<213> ORGANISM: Artificial Sequence
<220> FEATURE:
<223> OTHER INFORMATION: The sequence contains sequences from Homo sapiens and Mus musculus

<400> SEQUENCE: 29
gttttcccag tcacgac 17

<210> SEQ ID NO 30
<211> LENGTH: 21
<212> TYPE: DNA

<213> ORGANISM: Artificial Sequence
<220> FEATURE:
<223> OTHER INFORMATION: The sequence contains sequences from Homo sapiens and Mus musculus

<400> SEQUENCE: 30
agcggataat ttcacacagg a 21

<210> SEQ ID NO 31
<211> LENGTH: 42
<212> TYPE: DNA
<213> ORGANISM: Artificial Sequence
<220> FEATURE:
<223> OTHER INFORMATION: The sequence contains sequences from Homo sapiens and Mus musculus

<400> SEQUENCE: 31
aagcttgccg ccaccatggc tgtcctgggg ctgctcttct gc 42

<210> SEQ ID NO 32
<211> LENGTH: 46
<212> TYPE: DNA
<213> ORGANISM: Artificial Sequence
<220> FEATURE:
<223> OTHER INFORMATION: The sequence contains sequences from Homo sapiens and Mus musculus

<400> SEQUENCE: 32
ccgatgggcc cttggtggag gctgaggaga cggtgactga ggttcc 46

<210> SEQ ID NO 33
<211> LENGTH: 43
<212> TYPE: DNA
<213> ORGANISM: Artificial Sequence
<220> FEATURE:
<223> OTHER INFORMATION: The sequence contains sequences from Homo sapiens and Mus musculus

<400> SEQUENCE: 33
aagcttgccg ccaccatgaa gttgcctgtt aggctgttgg tgc 43

<210> SEQ ID NO 34
<211> LENGTH: 42
<212> TYPE: DNA
<213> ORGANISM: Artificial Sequence
<220> FEATURE:
<223> OTHER INFORMATION: The sequence contains sequences from Homo sapiens and Mus musculus

<400> SEQUENCE: 34
ggatccactc acgtttgatt tccagcttgg tcccccctcc ga 42

<210> SEQ ID NO 35
<211> LENGTH: 111
<212> TYPE: PRT
<213> ORGANISM: Mus musculus

<400> SEQUENCE: 35

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Ser Tyr
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr Lys Pro Asn Leu Met
```

```
    50                  55                  60

Ser Arg Leu Ser Ile Ser Lys Asp Ile Ser Lys Ser Gln Val Leu Phe
65                  70                  75                  80

Lys Leu Asn Ser Leu Gln Thr Asp Asp Thr Ala Thr Tyr Tyr Cys Val
                85                  90                  95

Thr Leu Asp Tyr Trp Gly Gln Gly Thr Ser Val Thr Val Ser Ser
            100                 105                 110


<210> SEQ ID NO 36
<211> LENGTH: 112
<212> TYPE: PRT
<213> ORGANISM: Mus musculus

<400> SEQUENCE: 36

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Phe Cys Phe Gln Thr
                85                  90                  95

Thr Tyr Val Pro Asn Thr Phe Gly Gly Gly Thr Lys Leu Glu Ile Lys
            100                 105                 110


<210> SEQ ID NO 37
<211> LENGTH: 131
<212> TYPE: PRT
<213> ORGANISM: Artificial Sequence
<220> FEATURE:
<223> OTHER INFORMATION: The sequence contains sequences from Homo
      sapiens and Mus musculus

<400> SEQUENCE: 37

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Arg Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Arg Asp Phe Ser Gly Ser Gly Ser Gly Thr Asp Phe Thr
                85                  90                  95

Leu Lys Ile Ser Arg Val Glu Ala Glu Asp Leu Gly Leu Tyr Phe Cys
            100                 105                 110

Phe Gln Thr Thr Tyr Val Pro Asn Thr Phe Gly Gly Gly Thr Lys Leu
        115                 120                 125

Glu Ile Lys
    130
```

```
<210> SEQ ID NO 38
<211> LENGTH: 130
<212> TYPE: PRT
<213> ORGANISM: Artificial Sequence
<220> FEATURE:
<223> OTHER INFORMATION: The sequence contains sequences from Homo
      sapiens and Mus musculus

<400> SEQUENCE: 38

Met Ala Val Leu Gly Leu Leu Phe Cys Leu Val Thr Phe Pro Ser Cys
1               5                   10                  15

Val Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Ser Ser Tyr Gly Val Ser Trp Val Arg Gln Pro Pro Gly Lys Gly Leu
    50                  55                  60

Glu Trp Leu Gly Val Ile Trp Gly Asp Gly Ser Thr Asn Tyr His Pro
65                  70                  75                  80

Asn Leu Met Ser Arg Leu Ser Ile Ser Lys Asp Ile Ser Lys Ser Gln
                85                  90                  95

Val Leu Phe Lys Leu Asn Ser Leu Gln Thr Asp Asp Thr Ala Thr Tyr
            100                 105                 110

Tyr Cys Val Thr Leu Asp Tyr Trp Gly Gln Gly Thr Ser Val Thr Val
        115                 120                 125

Ser Ser
    130


<210> SEQ ID NO 39
<211> LENGTH: 333
<212> TYPE: DNA
<213> ORGANISM: Mus musculus

<400> SEQUENCE: 39

caggtgcagc tgaaggagtc aggacctggc ctggtggcgc cctcacagag cctgtccatc      60

acatgcactg tctcagggtt ctcattaagc agctatggtg taagctgggt tcgccagcct     120

ccaggaaagg gtctggagtg gctgggagta atatggggtg acgggagcac aaattatcat     180

ccaaatctca tgtccagact gagtatcagc aaggatattt ccaagagcca agttctcttc     240

aaactgaata gtctgcaaac tgatgacaca gccacgtact actgtgtcac cttcgactac     300

tggggtcaag gaacctcagt caccgtctcc tca                                  333


<210> SEQ ID NO 40
<211> LENGTH: 336
<212> TYPE: DNA
<213> ORGANISM: Mus musculus

<400> SEQUENCE: 40

gatgttgtga tgacccaaac tccactctcc ctgcctgtca gtcttggaga tcaagcctcc      60

atctcttgca gatctagtca gagccttgta catagaaatg gaaacaccta tttacattgg     120

tacctgcaga agccaggcca gtctccaaag ctcctgatct acaaagtttc caaccgattt     180

tctggggtcc cagacaggtt cagtggcagt ggatcaggga cagatttcac actcaagatc     240

agcagagtgg aggctgagga tttgggactt tatttctgtt ttcaaactac atatgttccg     300

aacacgttcg gagggggac caagctggaa ataaaa                                336


<210> SEQ ID NO 41
```

-continued

<211> LENGTH: 43
<212> TYPE: DNA
<213> ORGANISM: Mus musculus

<400> SEQUENCE: 41
aagcttgccg ccaccatgaa gttgcctgtt aggctgttgg tgc 43

<210> SEQ ID NO 42
<211> LENGTH: 422
<212> TYPE: DNA
<213> ORGANISM: Artificial Sequence
<220> FEATURE:
<223> OTHER INFORMATION: The sequence contains sequences from Homo sapiens and Mus musculus

<400> SEQUENCE: 42
aagcttgccg ccaccatgaa gttgcctgtt aggctgttgg tgctgatgtt ctggattcct 60
gcttccagca gtgatgttgt gatgacccaa actccactct ccctgcctgt cagtcttgga 120
gatcaagcct ccatctcttg cagatctagt cagagccttg tacatagaaa tggaaacacc 180
tatttacatt ggtacctgca gaagccaggc cagtctccaa agctcctgat ctacaaagtt 240
tccaaccgat tttctggggt cccagacagg ttcagtggca gtggatcagg gacagatttc 300
acactcaaga tcagcagagt ggaggctgag gatttgggac tttatttctg ttttcaagac 360
tacatatgtt ccgaacacgt tcggaggggg gaccaagctg gaaatcaaac gtgagtggat 420
cc 422

<210> SEQ ID NO 43
<211> LENGTH: 42
<212> TYPE: DNA
<213> ORGANISM: Mus musculus

<400> SEQUENCE: 43
ggatccactc acgtttgatt tccagcttgg tcccccctcc ga 42

<210> SEQ ID NO 44
<211> LENGTH: 42
<212> TYPE: DNA
<213> ORGANISM: Mus musculus

<400> SEQUENCE: 44
aagctttccg ccaccatggc tgtcctgggg ctgctcttct gc 42

<210> SEQ ID NO 45
<211> LENGTH: 426
<212> TYPE: DNA
<213> ORGANISM: Artificial Sequence
<220> FEATURE:
<223> OTHER INFORMATION: The sequence contains sequences from Homo sapiens and Mus musculus

<400> SEQUENCE: 45
aagctttccg ccaccatggc tgtccctggg gctgctcttc tgcctggtga cattaccaag 60
ctgtgtcctg tcccaggtgc agctgaagga gtcaggacct ggcctggtgg agcctcacag 120
agcctgtcca tcacatgcac tgtctcaggg ttctcattaa gcagctatgg tgtaagctgg 180
gttcgccagc ccaggaaagg gtctggagtg gctgggagta atatggggtg acgggagcac 240
aaattatcat ccaaatctca tgtccagact gagtatcagc aaggatattt ccaagagcaa 300
gttctcttca aactgaatag tctgcaaact gatgacacag ccacgtacta ctgtgtcacc 360
ttggactact ggggtcaaag gaacctccag tcaccgtctc ctcagcctcc accacgggcc 420

```
catcgg                                                                   426


<210> SEQ ID NO 46
<211> LENGTH: 46
<212> TYPE: DNA
<213> ORGANISM: Mus musculus

<400> SEQUENCE: 46

ccgatgggcc cttggtggag gctgaggaga cggtgactga ggttcc                        46


<210> SEQ ID NO 47
<211> LENGTH: 112
<212> TYPE: PRT
<213> ORGANISM: Artificial Sequence
<220> FEATURE:
<223> OTHER INFORMATION: The sequence contains sequences from Homo
      sapiens and Mus musculus

<400> SEQUENCE: 47

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Arg Asp Phe Ser Gly Ser Gly Ser Gly Thr Asp Phe Thr Leu Lys Ile
65                  70                  75                  80

Ser Arg Val Glu Ala Glu Asp Leu Gly Leu Tyr Phe Cys Phe Gln Thr
                85                  90                  95

Thr Tyr Val Pro Asn Thr Phe Gly Gly Gly Thr Lys Leu Glu Ile Lys
            100                 105                 110


<210> SEQ ID NO 48
<211> LENGTH: 111
<212> TYPE: PRT
<213> ORGANISM: Artificial Sequence
<220> FEATURE:
<223> OTHER INFORMATION: The sequence contains sequences from Homo
      sapiens and Mus musculus

<400> SEQUENCE: 48

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Ser Tyr
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Pro Asn Leu Met
    50                  55                  60

Ser Arg Leu Ser Ile Ser Lys Asp Ile Ser Lys Ser Gln Val Leu Phe
65                  70                  75                  80

Lys Leu Asn Ser Leu Gln Thr Asp Asp Thr Ala Thr Tyr Tyr Cys Val
                85                  90                  95

Thr Leu Asp Tyr Trp Gly Gln Gly Thr Ser Val Thr Val Ser Ser
            100                 105                 110
```